(12) United States Patent
Ohnmacht

(10) Patent No.: US 6,403,601 B1
(45) Date of Patent: Jun. 11, 2002

(54) N-(2-PHENYL-4-PIPERIDINYBUTYL)-5,6,7,8-TETRAHYDRO-1-NAPHTHALENECARBOXAMIDES AND THEIR USE AS NEUROKININ 1 (NK1) AND/OR NEUROKININ 2 (NK2) RECEPTOR ANTAGONISTS

(75) Inventor: Cyrus John Ohnmacht, Wilmington, DE (US)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 09/857,833

(22) PCT Filed: Dec. 6, 1999

(86) PCT No.: PCT/GB99/04118

§ 371 (c)(1),
(2), (4) Date: Jun. 7, 2001

(87) PCT Pub. No.: WO00/34243

PCT Pub. Date: Jun. 15, 2000

(30) Foreign Application Priority Data

Dec. 9, 1998 (GB) .............................. 9826941

(51) Int. Cl.$^7$ .................... C07D 401/04; A61K 31/505; A61K 31/45
(52) U.S. Cl. ....................... 514/274; 514/327; 546/188; 544/316
(58) Field of Search ................................ 546/188, 205, 546/206; 544/302, 316; 514/316, 318, 319, 270, 274, 327

(56) References Cited

U.S. PATENT DOCUMENTS 5,350,852 A * 9/1994 Emonds-Alt et al. ....... 544/336
5,789,422 A   8/1998 Aslanian et al.

FOREIGN PATENT DOCUMENTS

| EP | 0 625 509 A | 11/1994 |
| EP | 0 630 887 A | 12/1994 |
| WO | WO 98 07722 A | 2/1998 |

* cited by examiner

*Primary Examiner*—John M. Ford
(74) *Attorney, Agent, or Firm*—Kenneth F. Mitchell

(57) ABSTRACT

Compounds of formula (I), wherein $R^2$ is a 5,6,7,8-tetrahydronaphth-1-yl group which may be substituted (the remaining groups defined herein), and pharmaceutical compositions containing the compounds and methods of using the compounds in the treatment of a condition where antagonism of the NK1 and/or NK2 receptors is beneficial.

(I)

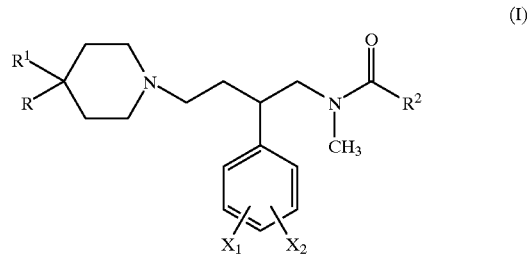

9 Claims, No Drawings

N-(2-PHENYL-4-PIPERIDINYBUTYL)-5,6,7,8-TETRAHYDRO-1-NAPHTHALENECARBOXAMIDES AND THEIR USE AS NEUROKININ 1 (NK1) AND/OR NEUROKININ 2 (NK2) RECEPTOR ANTAGONISTS

This invention relates to tetrahydronaphthalenecarboxamide compounds N-substituted by a substituted piperidinylbutyl group, to pharmaceutical compositions containing such compounds, as well as to their uses and processes for their preparation. These compounds antagonize the pharmacological actions of the endogenous neuropeptide tachykinins known as neurokinins, particularly at the neurokinin1 (NK1) and the neurokinin 2 (NK2) receptors. These compounds are useful whenever such antagonism is desired. Thus, such compounds are of value in the treatment of those diseases in which Substance P and Neurokinin A are implicated, for example, in the treatment of asthma, anxiety, depression, emesis, urinary incontinence and related conditions.

The mammalian neurokinins comprise a class of peptide neurotransmitters which are found in the peripheral and central nervous systems. The three principal neurokinins are Substance P (SP), Neurokinin A (NKA) and Neurokinin B (NKB).

There are also N-terminally extended forms of at least NKA. At least three receptor types are known for the three principal neurokinins. Based upon their relative selectivities favoring the neurokinin agonists SP, NKA and NKB, the receptors are classified as neurokinin 1 (NK1), neurokinin 2 (NK2) and neurokinin 3 (NK3) receptors, respectively. In the periphery, SP and NKA are localized in C-afferent sensory neurons, which neurons are characterized by non-myelinated nerve endings known as C-fibers, and are released by selective depolarization of these neurons, or selective stimulation of the C-fibers. C-Fibers are located in the airway epithelium, and the tachykinins are known to cause profound effects which clearly parallel many of the symptoms observed in asthmatics. The effects of release or introduction of tachykinins in mammalian airways include bronchoconstriction, increased microvascular permeability, vasodilation, increased mucus secretion and activation of mast cells. Thus, the tachykinins are implicated in the pathophysiology and airway hyperresponsiveness observed in asthmatics; and blockade of the action of released tachykinins may be useful in the treatment of asthma and related conditions. A cyclopeptide antagonist (FK-224) selective for both NK1 and NK2 receptors has demonstrated clinical efficacy in human patients suffering from asthma and chronic bronchitis. M. Ichinose, et al., *Lancet*, 1992, 340, 1248.

In particular the N-substituted tetrahydronaphthalenecarboxamide compounds of the present invention show a high degree of NK1 and/or mixed NK1/NK2 receptor antagonist activity. Additionally, by manipulation of the substituents on the naphthalene and piperidine rings of the formula (I), the ratio of activity at the NK1 and NK2 receptors can be modified as desired, affording compounds that are predominantly active at NK1 receptors or affording compounds with a balanced activity and, as such, are particularly useful when combined antagonism of both receptors is desired. In particular, the compounds of the present invention also possess a high degree of NK1 and/or mixed NK1/NK2 antagonism upon oral administration.

Accordingly the present invention provides the compounds of the formula (I):

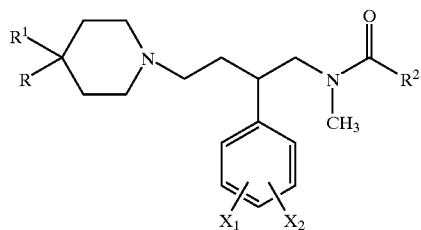

wherein:

R is hydrogen, hydroxy, $C_{1-6}$alkoxy, $C_{1-6}$alkanoyloxy, $C_{1-6}$alkanoyl, $C_{1-6}$alkoxycarbonyl, $C_{1-6}$alkanoylamino, $C_{1-6}$alkyl, carbamoyl, $C_{1-6}$alkylcarbamoyl or di-$C_{1-6}$alkylcarbamoyl;

$R^1$ is a phenyl group substituted in the ortho position by $C_{1-6}$alkylthio, $C_{1-6}$alkyl-sulfinyl, $C_{1-6}$alkylsulfonyl, trifluoromethylthio, trifluoromethylsulfinyl, $C_{1-6}$alkane-sulfonamido, $C_{1-6}$alkanoyl, $C_{1-6}$alkoxycarbonyl, succinamido, carbamoyl, $C_{1-6}$alkyl-carbamoyl, di-$C_{1-6}$alkylcarbamoyl, $C_{1-6}$alkoxy-$C_{1-6}$alkylcarbamoyl, $C_{1-6}$alkanoylamino, ureido, $C_{1-6}$ureido, di-$C_{1-6}$alkylureido, amino, $C_{1-6}$alkylamino or di-$C_{1-6}$alkylamino, which phenyl group optionally may bear further substituents;

or $R^1$ is a group of the formula (1a):

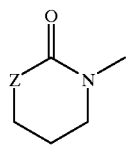

wherein Z is NH or $CH_2$.

$R^2$ is an optionally substituted 5,6,7,8-tetrahydronaphth-1-yl group and $X_1$ and $X_2$ are independently hydrogen or halo, provided that at least one of $X_1$ or $X_2$ is halo; and pharmaceutically acceptable salts thereof.

Suitable further substituents, which are optional, for $R^1$ when it is an ortho-substituted phenyl ring include $C_{1-6}$alkylthio for example methylthio or ethylthio; $C_{1-6}$alkylsulfinyl for example methylsulfinyl, ethylsulfinyl or propoxysulfinyl; $C_{1-6}$alkylsulfonyl for example methylsulfonyl or ethylsulfonyl; carboxy; $C_{1-6}$alkoxycarbonyl for example methoxycarbonyl; $C_{1-6}$alkanoyl for example acetyl or propionyl; nitro; amino; $C_{1-6}$alkylamino for example methylamino or ethylamino; di-$C_{1-6}$alkylamino where the alkyl groups may be the same or different, for example dimethylamino; trifluoromethyl; $CF_3S(O)_x$ wherein x is 0, 1 or 2, for example trifluoromethylthio, trifluoromethylsulfinyl or trifluoromethylsulfonyl; $C_{1-6}$alkanoylamino for example acetylamino or propionylamino; $C_{1-6}$alkalkylsulphonamido for example methylsulphonamido; ureido; $C_{1-6}$alkylureido for example methylureido (MeNHCONH—), di-$C_{1-6}$alkylureido for example dimethylureido (Mc,NCONH—); carbamoyl; $C_{1-6}$alkylcarbamoyl for example methylcarbamoyl; di-$C_{1-6}$alkylcarbamoyl where the alkyl groups may be the same or different, for example dimethylcarbamoyl; and $C_{1-6}$alkyl for example methyl substituted by any of the hereinabove substituents.

Suitable substituents, which are optional, for the 5,6,7,8-tetrahydronaphth-1-yl group include hydroxy; cyano; nitro;

trifluoromethoxy; trifluoromethyl; $C_{1-6}$alkylsulfonyl for example methylsulphonyl; halo for example chloro, bromo, fluoro or iodo; $C_{1-6}$alkoxy for example methoxy, ethoxy or propoxy; methylenedioxy (—OCH$_2$O—), $C_{1-6}$alkyl for example methyl or ethyl; $C_{2-6}$alkenyl for example ethenyl, prop-1-enyl or prop-2-enyl; $C_{2-6}$alkynyl for example ethynyl; carboxy, $C_{1-6}$alkoxy-carbonyl for example methoxycarbonyl; carbamoyl; $C_{1-6}$alkylcarbamoyl for example methylcarbamoyl or ethylcarbamoyl; di-$C_{1-6}$alkylcarbamoyl for example di-methylcarbamoyl; $C_{1-6}$alkanoyl for example acetyl or propionyl; $C_{1-6}$alkanoylamino for example acetylamino or propionylamino; aminosulfonyl; and $C_{1-6}$alkyl for example methyl substituted by any of the hereinabove substituents.

When $R^1$ is a phenyl ring it is ortho-substituted by $C_{1-6}$alkylthio for example methylthio; $C_{1-6}$alkylsulfinyl for example methylsulfinyl, ethylsulfinyl or propylsulfinyl; $C_{1-6}$alkylsulfonyl for example methylsulfonyl or ethylsulfonyl; trifluoromethylthio; trifluoromethylsulfinyl; $C_{1-6}$alkanesulfonamido for example methanesulfonamido; $C_{1-6}$alkanoyl for example acetyl or propionyl; $C_{1-6}$alkoxy-carbonyl for example methoxycarbonyl; succinamido; carbamoyl; $C_{1-6}$alkylcarbamoyl for example methylcarbamoyl; di-$C_{1-6}$alkylcarbamoyl for example dimethylcarbamoyl; $C_{1-6}$alkoxy-$C_{1-6}$alkylcarbamoyl for example N-methoxy, N-methylcarbamoyl; $C_{1-6}$alkanoylamino for example acetylamino; ureido, $C_{1-6}$ureido for example methylureido; di-$C_{1-6}$alkylureido for example dimethylureido; amino; $C_{1-6}$alkylamino for example methylamino or ethylamino; or di-$C_{1-6}$alkylamino for example dimethylamino.

Preferred values for the ortho-substituent are methylsulfinyl, ethylsulfinyl, propylsulfinyl, methylsulfonyl, trifluoromethylthio, trifluoromethylsulfinyl, methanesulfonamido, acetyl, methoxycarbonyl, succinamido, carbamoyl, methylcarbamoyl, dimethylcarbamoyl, N-methoxy, N-methylcarbamoyl, acetylarnino, ureido, methylureido, dimethylureido, amino, methylamino or dimethylamino.

In particular the ortho-substituent is methylsulfinyl, methylsulfonyl, methylureido, dimethylureido, amino, methylamino or dimethylamino. Of these methylsulfinyl is particularly preferred.

Favourably the ortho-substituted phenyl ring is not substituted further or is substituted by up to three optional substituents. In particular the ortho-substituted phenyl ring is not substituted further or is substituted at the 4-position, that is the position para- to the bond with the piperidine ring, so forming a 2, 4-disubstituted phenyl group, preferably a 2-MeSO, 4-substituted phenyl group.

Preferred substituents if present, for the ortho-substituted phenyl ring, are methyl, methoxy, acetyl, acetylamino, methoxycarbonyl, methanesulfonylamino, methyl-sulfinyl, methylsulfonyl, trifluoromethyl, trifluoromethylthio, trifluoromethylsulfinyl, bromo, fluoro, chloro, hydroxy, carbamoyl, methylcarbamoyl, dimethylcarbamoylmethylureido and dimethylureido. In particular these preferred substituents may be at the 4-position of the phenyl ring.

Thus a preferred class of compounds is that wherein $R^1$ is of the formula (Ib):

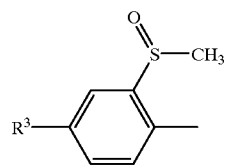

(Ib)

wherein $R^3$ is hydrogen, $C_{1-6}$alkoxy for example methoxy or ethoxy, halo for example bromo, chloro or fluoro, $C_{1-6}$alkylsulfinyl for example methylsulfinyl or carboxy.

In particular $R^3$ is hydrogen, $C_{1-6}$alkoxy or halo.

Most particularly $R^3$ is hydrogen, methoxy or fluoro.

In another aspect $R^1$ is a group of the formula (Ia). In one aspect Z is NH so forming a tetrahydropyrimidone ring. In another aspect Z is methylene so forming a tetrahydropyridone ring.

The compounds of the invention have a number of chiral centres. It is preferred that the ortho-methylsulfinyl substituent, if present, has the stereochemistry depicted in formula (Ic):

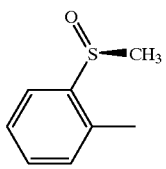

(Ic)

Favourably the 5,6,7,8-tetrahydronaphth-1-yl group (Id):

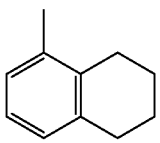

(Id)

is unsubstituted or is substituted by up to three substituents. Preferred substituents for the 5,6,7,8-tetrahydronaphth-1-yl group include cyano; nitro; $C_{1-6}$alkylsulfonyl for example methylsulphonyl; halo for example chloro, bromo, fluoro or iodo; $C_{1-6}$alkoxy for example methoxy, ethoxy, n-propoxy or isopropoxy; methylenedioxy (—OCH$_2$O—); $C_{1-6}$alkyl for example methyl or ethyl; $C_{2-6}$alkenyl for example prop-2-enyl; $C_{2-6}$alkynyl for example ethynyl; carboxy, carbamoyl; $C_{1-6}$alkyl-carbamoyl for example methylcarbamoyl; di-$C_{1-6}$alkylcarbamoyl for example di-methylcarbamoyl; $C_{1-6}$alkanoyl for example acetyl; $C_{1-6}$alkanoylamino for example acetylamino; aminosulfonyl; and cyano$C_{1-6}$alkyl for example cyanomethyl.

More preferred substituents for the 5,6,7,8-tetrahydronaphth-1-yl group are cyano, methoxy, ethoxy, isopropoxy, fluoro, bromo, chloro, iodo, nitro, cyanomethyl, carboxy, carbamoyl, ethynyl, methyl, dimethylcarbamoyl, methylsulfonyl, aminosulfonyl, prop-2-enyl, acetyl and acetylamino.

In particular the 5,6,7,8-tetrahydronaphth-1-yl group may be substituted by up to two substituents selected from cyano, methoxy, fluoro and nitro. A particularly preferred substitution pattern for the 5,6,7,8-tetrahydronaphth-1-yl group is 3-cyano. A further particularly preferred substitution pattern is 3-cyano, 2-methoxy. Another particularly preferred substitution pattern is 2,3-dimethoxy. Another particularly preferred substitution pattern is 3,4-dimethoxy.

The compounds of the present invention possess a number of chiral centres, at —CH(Ph-$X_1,X_2$)—, and possibly in the optional substituents (for example the MeSO—substituent) on either (or both) of the phenyl (when $R^1$ is an ortho-substituted phenyl ring) and the tetrahydronaphth-1-yl groups. The present invention covers all isomers, diastereoisomers and mixtures thereof that antagonise NK1 and/or NK2.

The preferred configuration at —CH(Ph-$X_1,X_2$)— is shown in formula (Ie) hereinbelow:

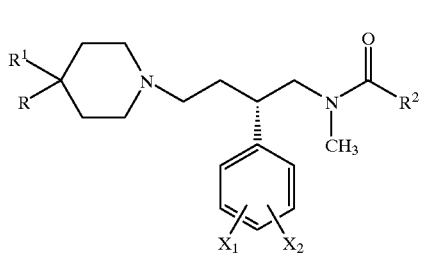

(Ie)

Favourably $X_1$ and $X_2$ are both chloro. In a preferred aspect Ph-$X_1,X_2$ is 3,4-dichlorophenyl.

R is hydrogen; hydroxy; $C_{1-6}$alkoxy for example methoxy or ethoxy; $C_{1-6}$alkanoyloxy for example acetyloxy or propionyloxy; $C_{1-6}$alkanoyl for example acetyl or propionyl; $C_{1-6}$alkoxycarbonyl for example methoxycarbonyl or ethoxycarbonyl; $C_{1-6}$alkanoylamino for example acetylamino; $C_{1-6}$alkyl for example methyl or ethyl; carbamoyl; $C_{1-6}$alkylcarbamoyl for example methylcarbamoyl or ethylcarbamoyl or di-$C_{1-6}$alkylcarbamoyl for example dimethylcarbamoyl.

Preferably R is hydrogen, hydroxy, methoxycarbonyl, methylcarbamoyl or dimethylcarbamoyl. More preferably R is hydrogen or hydroxy; most preferably R is hydrogen.

A preferred class of compounds is that of the formula (II):

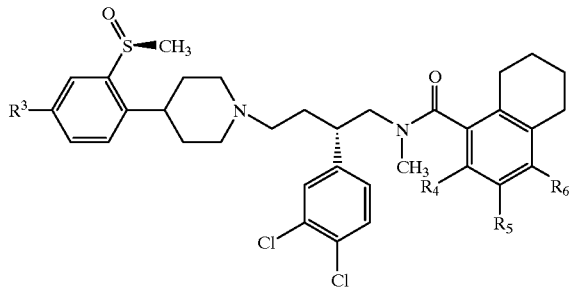

(II)

wherein $R^3$ is as hereinbefore defined and $R^4$–$R^6$ are selected from hydrogen, cyano, nitro, methoxy and fluoro. In one particular aspect, in the compounds of the formula (II), $R^3$ is hydrogen, methoxy or fluoro, $R^4$ is hydrogen or fluoro, $R^6$ is hydrogen, and $R^5$ is methoxy, cyano or nitro. In another particular aspect, $R^3$ is hydrogen, methoxy or fluoro, $R^4$ and $R^5$ are hydrogen, and $R^6$ is cyano or nitro. In a further particular aspect, $R^3$ is hydrogen, methoxy or fluoro, $R^4$ is methoxy, $R^6$ is hydrogen, and $R^5$ is cyano or nitro.

Particular compounds of this invention are provided as the Examples hereinbelow;

N-[2-(S)-(3,4-dichlorophenyl)-4-[4-[(S)-2-(methylsulfinyl)phenyl]-1-piperidinyl]butyl]-N-methyl-3-cyano-2-methyl-5,6,7,8-tetrahydro-1-naphthamide;

N-[2-(S)-(3,4-dichlorophenyl)-4-[4-[(S)-2-(methylsulfinyl)phenyl]-1-piperidinyl]butyl]-N-methyl-3-cyano-2-ethyl-5,6,7,8-tetrahydro-1-naphthamide;

N-[2-(S)-(3,4-dichlorophenyl)4-[4-[(S)-2-(methylsulfinyl)phenyl]-1-piperidinyl]butyl]-N-methyl-3-methoxy-2-methyl-5,6,7,8-tetrahydro-1-naphthamide;

N-[2-(S)-(3,4-dichlorophenyl)4-[4-[(S)-2-(methylsulfinyl)phenyl]-1-piperidinyl]butyl]-N-methyl-2-methoxy-3-methyl-5,6,7,8-tetrahydro-1-naphthamide;

N-[2-(S)-(3,4-dichlorophenyl)-4-[4-[(S)-2-(methylsulfinyl)phenyl]-1-piperidinyl]butyl]-N-methylsulfonyl-3-cyano-2-methoxy-5,6,7,8-tetrahydro-1-naphthamide; and N-(4-[4-(tetrahydro-2-oxo-1(2H)-pyrimidinyl)-4-methylarminocarbonyl)-1-piperidinyl]-2-(3,4-dichlorophenyl)butyl)-N-methyl-3-cyano-2-methoxy-5,6,7,8-tetrahydro-1-naphthamide.

Pharmaceutically acceptable salts of the compounds of the formula (I) include those made with inorganic or organic acids which afford a physiologically acceptable anion, such as with, for example, hydrochloric, hydrobromic, sulfuric, phosphoric, methanesulfonic, sulfamic, para-toluenesulfonic, acetic, citric, lactic, tartaric, malonic, fumaric, ethanesulfonic, benzenesulfonic, cyclohexylsulfamic, salicyclic and quinic acids.

In order to use a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt and pharmaceutically acceptable carrier.

The pharmaceutical compositions of this invention may be administered in standard manner for the disease condition that it is desired to treat, for example by oral, topical, parenteral, buccal, nasal, vaginal or rectal administration or by inhalation or insufflation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to herein.

The pharmaceutical compositions of this invention will normally be administered to humans so that, for example, a daily dose of 0.01 to 25 mg/kg body weight (and preferably of 0.1 to 5 mg/kg body weight) is received. This daily dose may be given in divided doses as necessary, the precise amount of the compound received and the route of administration depending on the weight, age and sex of the patient being treated and on the particular disease condition being treated according to principles known in the art.

Typically unit dosage forms will contain about 1 mg to 500 mg of a compound of this invention. For example a tablet or capsule for oral administration may conveniently contain up to 250 mg (and typically 5 to 100 mg) of a compound of the formula (I) or a pharmaceutically acceptable salt thereof. In another example, for administration by inhalation, a compound of the formula (I) or a pharmaceutically acceptable salt thereof may be administered in a daily dosage range of 5 to 100 mg, in a single dose or divided into two to four daily doses. In a further example, for administration by intravenous or intramuscular injection or infusion, a sterile solution or suspension containing up to 10% w/w (and typically 5% w/w) of a compound of the formula (I) or a pharmaceutically acceptable salt thereof may be used.

Therefore in a further aspect, the present invention provides a compound of the formula (I) or a pharmaceutically acceptable salt thereof for use in a method of therapeutic treatment of the human or animal body.

In yet a further aspect the present invention provides a method of treating a disease condition wherein antagonism of the NK1 and/or NK2 receptors is beneficial which comprises administering to a warm-blooded animal an effective amount of a compound of the formula (I) or a pharmaceutically acceptable salt thereof. The present invention also provides the use of a compound of the formula (I) or a pharmaceutically acceptable salt thereof in the preparation of a medicament for use in a disease condition wherein antagonism of the NK1 and/or NK2 receptors is beneficial.

The compounds of the formula (I) and their pharmaceutically acceptable salts may be made by processes as described and exemplified herein and by processes similar thereto and by processes known in the chemical art. If not commercially available, starting materials for these processes may be made by procedures which are selected from the chemical art using techniques which are similar or analogous to the synthesis of known compounds.

In another aspect the present invention provides a process for preparing a compound of the formula (I) or a pharmaceutically acceptable salt thereof which process comprises:
a) reacting a compound of the formula (III) with a compound of the formula (IV):

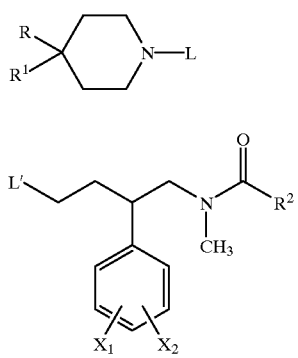

wherein R, $R_1$, $R^2$, $X_1$ and $X_2$ are as hereinbefore defined; and L and L' are groups such that reductive amination of the compounds of the formulae (III) and (IV) forms a N—C bond; or b) reacting a compound of the formula (V) with a compound of the formula (VI):

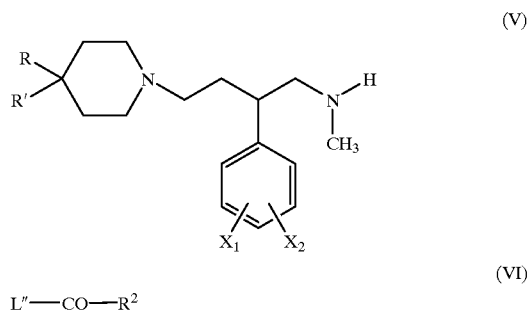

wherein R, $R^1$, $R^2$, $X_1$ and $X_2$ are as hereinbefore defined; and L" is a leaving group; wherein any other functional group is protected, if necessary, and:

i) removing any protecting groups;
ii) optionally forming a pharmaceutically acceptable salt.

Protecting groups may in general be chosen from any of the groups described in the literature or known to the skilled chemist as appropriate for the protection of the group in question, and may be introduced and removed by conventional methods; see for example Protecting Groups in Organic Chemistry; Theodora W. Greene. Methods of removal are chosen so as to effect removal of the protecting group with minimum disturbance of groups elsewhere in the molecule.

It will also be appreciated that certain of the various optional substituents in the compounds of the formula (I) may be introduced by standard aromatic substitution reactions or generated by conventional functional group modifications either prior to or immediately following the processes described hereinabove. The reagents and reaction conditions for such procedures are well known in the chemical art.

Pharmaceutically acceptable salts may be prepared from the corresponding acid in conventional manner. Non-pharmaceutically acceptable salts may be useful as intermediates and as such are another aspect of the present invention.

It is well known in the art how to prepare optically-active forms (for example, by resolution of the racemic form or by synthesis from optically-active starting materials) and how to determine the NK1 and NK2 antagonist properties by the standard tests known in the art and those described hereinafter.

The compounds of the formulae (III) and (IV) are reacted under conditions of reductive amination. Typically in the compounds of the formula (III) L is hydrogen.

Typically in the compounds of the formula (IV) L' is an oxo group so forming an aldehyde moiety. The reaction is typically performed at a non-extreme temperature, for example 0–100° C., suitably ambient temperature in a substantially inert solvent for example dichloromethane. Typical reducing agents include borohydrides such as sodium cyanoborohydride.

The compounds of the formula (III) are known or made be prepared in conventional manner. The compounds of the formula (IV) may be prepared, for example, by reacting a compound of the formula (VI) with a compound of the formula (VII):

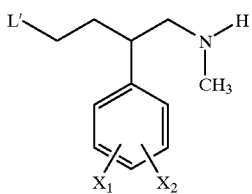

(VII)

wherein L', $X_1$ and $X_2$ are as hereinbefore defined under conventional acylation conditions.

The compounds of the formulae (V) and (VI) may be reacted under conventional acylation conditions wherein L"CO—$R^2$ is an acid or an activated acid derivative. Such activated acid derivatives are well known in the literature. They may be formed in situ from the acid or they may be prepared, isolated and subsequently reacted. Typically L" is chloro thereby forming the acid chloride. Typically the acylation reaction is performed in the presence of a non-nucleophilic base, for example di-isopropylethylamine, in a substantially inert solvent at a non-extreme temperature.

The compounds of the formula (VII) are known or may be prepared in conventional manner. Compounds of the formula (IV) and certain compounds of the formula (VI) are novel and form part of the present invention. In particular the compounds of the formula (VI) wherein the aromatic ring of the 5,6,7,8-tetrahydronaphth-1-yl group is substituted by at least one group selected from cyano, nitro, methoxy and fluoro are novel. For example, a preferred class of novel compounds is of the formula (VIII):

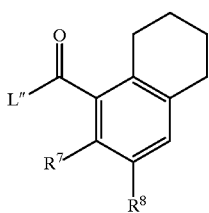

(VIII)

wherein L" is as hereinbefore defined; preferably L" is hydrogen or a leaving group such as chloro; $R^7$ is hydrogen or methoxy and $R^8$ is hydrogen, methoxy or cyano with the proviso that $R^7$ and $R^8$ are not both hydrogen when L" is hydrogen.

In another aspect the present invention provides a compound of the formulae (IX):

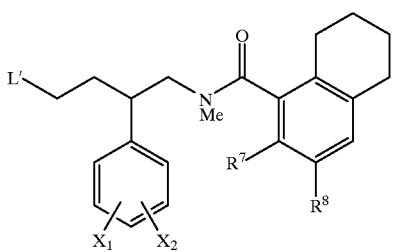

(IX)

wherein $X^1$, $X^2$ and L' are as hereinbefore defined, $R^7$ is hydrogen or methoxy and $R^8$ is hydrogen, methoxy or cyano.

The following biological test methods, data and Examples serve to illustrate and further describe the invention.

The utility of a compound of the invention or a pharmaceutically acceptable salt thereof (hereinafter, collectively referred to as a "Compound") may be demonstrated by standard tests and clinical studies, including those disclosed in the publications described below.

SP Receptor Binding Assay (Test A)

The ability of a Compound of the invention to antagonize the binding of SP at the NK1 receptor may be demonstrated using an assay using the human NK1 receptor expressed in Mouse Erythroleukemia (MEL) cells. The human NK1 receptor was isolated and characterized as described in: B. Hopkins, et al. "Isolation and characterization of the human lung NK1 receptor cDNA" *Biochem. Biophys. Res. Comm.*, 1991, 180, 1110–1117; and the NK1 receptor was expressed in Mouse Erythroleukemia (MEL) cells using a procedure similar to that described in Test B below.

Neurokinin A (NKA) Receptor Binding Assay (Test B)

The ability of a Compound of the invention to antagonize the binding of NKA at the NK2 receptor may be demonstrated using an assay using the human NK2 receptor expressed in Mouse Erythroleukermia (MEL) cells, as described in: Aharony, D., et al. "Isolation and Pharmacological Characterization of a Hampster Neurokinin A Receptor CDNA" *Molecular Pharinacology*, 1994, 45, 9–19.

The selectivity of a Compound for binding at the NK1 and the NK2 receptors may be shown by determining its binding at other receptors using standard assays, for example, one using a tritiated derivative of NKB in a tissue preparation selective for NK3 receptors. In general, the Compounds of the invention which were tested demonstrated statistically significant binding activity in Test A and Test B with a $K_i$ of 1 microM or much less typically being measured.

Rabbit Pulmonary Artery: NK1 In Vitro Functional Assay (Test C)

The ability of a Compound of the invention to antagonize the action of the agonist Ac-[$Arg^6$, $Sar^9$, $Met(O_2)^{11}$] Substance P (6-11), ASMSP, in a pulmonary tissue may be demonstrated as follows.

Male New Zealand white rabbits are euthanized via i.v. injection into an ear vein with 60 mg/kg Nembutal (50 mg/mL). Preceding the Nembutal into the vein is Heparin (1000 units/mL) at 0.0025 ml/kg for anticoagulant purposes. The chest cavity is opened from the top of the rib cage to the sternum and the heart, lungs and part of the trachea are removed. The pulmonary arteries are isolated from the rest of the tissues and cut in half to serve as pairs.

The segments are suspended between stainless steel stirrups, so as not to remove any of the endothelium, and placed in water-jacketed (37° C.) tissue baths containing physiological salt solution of the following composition (mM): NaCl, 118.0; KCl, 4.7; $CaCl_2$, 1.8; $MgCl_2$, 0.54; $NaH_2PO_4$, 1.0; $NaHCO_3$, 25.0; glucose, 11.0; indomethacin, 0.005(to inhibit cyclooxygenase); and dl-Propranolol, 0.00l (to block β receptors); gassed continuously with 95% $O_2$-5% $CO_2$. Responses are measured on a Grass polygraph via Grass FT-03 transducers and the electrical signals (data) acquired using a $Mi^2$ software/hardware system for subsequent conversion to measures of relaxation.

Initial tension placed on each tissue is 2 grams, which is maintained throughout the 1.0 hour equilibration period. Tissues are washed with the physiological salt solution at 15 minute intervals. At the 30 and 45 minute wash the following treatments are added: $1 \times 10^{-6}$M Thiorphan (to block E.C.3.4.24.11), $3 \times 10_{-8}$M (S)-N-[2-(3,4-Dichlorophenyl)-4-[4-oxoperhydropyrimidin-1-yl)piperidino]butyl]-N-methylbenzamide (to block $NK_2$ receptors), and the given concentration of the Compound being tested. At the end of the 1.0 hour equilibration, $1 \times 10_{-6}$M L-Phenylephrine hydrochloride is added for 1.0 hour. At the end of the 1.0 hour, a dose relaxation curve to ASMSP is done. Each tissue is treated as a individual and is considered finished when it fails to relax further for 2 consecutive doses. When this section of the protocol is complete, $1 \times 10_{-3}$M Papaverine is added for maximum relaxation.

For non-competitive antagonists, the percent inhibition of relaxation is determined at a given concentration of the antagonist. Percent inhibition is determined when a tested Compound produces a statistically significant (p<0.05) reduction of the total relaxation which is calculated using the total relaxation as a percent of the control value. Potencies of competitive Compounds are determined by calculating the apparent dissociation constants ($K_B$) for each concentration tested using the standard equation:

$$K_B=[\text{antagonist}]/(\text{dose ratio} -1)$$

where dose ratio antilog[(agonist –log molar $EC_{50}$ without Compound)–(–log molar $EC_{50}$ with Compound)]. The $K_B$ values may be converted to the negative logarithms and expressed as –log molar $K_B$ (i.e. $PK_B$). For this evaluation, complete concentration-response curves for agonist obtained in the absence and presence of the Compound tested using paired pulmonary artery rings. The potency of the agonist is determined at 50% of its own maximum relaxation in each curve. The $EC_{50}$ values are converted to negative logarithms and expressed as –log molar $EC_{50}$.

NK2 In Vitro Functional Assay (Test D)

The ability of a Compound of the invention to antagonize the action of the agonist [β-ala$^8$] NKA (4–10), BANK, in a pulmonary tissue may be demonstrated as follows. Male New Zealand white rabbits are euthanized via i.v. injection into an ear vein with 60 mg/kg Nembutal (50 mg/mL). Preceding the Nembutal into the vein is Heparin (1000 units/mL) at 0.0025 mL/kg for anticoagulant purposes. The chest cavity is opened from the top of the rib cage to the sternum and a small incision is made into the heart so that the left and right pulmonary arteries can be cannulated with polyethylene tubing (PE260 and PE190 respectively). The pulmonary arteries are isolated from the rest of the tissues, then rubbed over an intimal surface to remove the endothelium, and cut in half to serve as pairs. The segments are suspended between stainless steel stirrups and placed in water-jacketed (37.0° C.) tissue baths containing physiological salt solution of the following composition (mM): NaCl, 118.0; KCl, 4.7; $CaCl_2$, 1.8; $MgCl_2$, 0.54; $NaH_2PO_4$, 1.0; $NaHCO_3$, 25.0; glucose, 11.0; and indomethacin, 0.005 (to inhibit cyclooxygenase); gassed continuously with 95% $O_2$-5% $CO_2$. Responses are measured on a Grass polygraph via Grass FT-03 transducers and the electrical signals (data) acquired using a $Mi^2$ software/hardware system for subsequent conversion to measures of contraction.

Initial tension placed on each tissue is 2 grams, which is maintained throughout the 45 minute equilibration period. Tissues are washed with the physiological salt solution at 15 minute intervals. After the 45 minute equilibration period, $3 \times 10^{-2}$M KCl is given for 60 minutes to test the viability of the tissues. The tissues are then washed extensively for 30 minutes. The concentration of the Compound being tested is then added for 30 minutes. At the end of the 30 minutes, a cumulative dose response curve to BANK is performed. Each tissue is treated as a individual and is considered finished when it fails to contract further for 2 consecutive doses. When this section of the protocol is complete, $3 \times 10^{-2}$M $BaCl_2$ is added for maximum contraction.

For non-competitive antagonists, the percent inhibition of contraction is determined at a given concentration of the antagonist Percent inhibition is determined when a tested Compound produces a statistically significant (p<0.05) reduction of the total contraction which is calculated using the total contraction as a percent of the control value. Potencies of competitive Compounds are determined by calculating the apparent dissociation constants ($K_B$) for each concentration tested using the standard equation:

$$K_B=[\text{antagonist}]/(\text{dose ratio} -1)$$

where dose ratio=antilog[(agonist –log molar $EC_{50}$ without Compound)–(–log molar $EC_{50}$ with Compound)]. The $K_B$ values may be converted to the negative logarithms and expressed as –log molar $K_B$ (i.e. $pK_B$). For this evaluation, complete concentration-response curves for agonist obtained in the absence and presence of the Compound tested using paired pulmonary artery rings. The potency of the agonist is determined at 50% of its own maximum contraction in each curve. The $EC_{50}$ values are converted to negative logarithms and expressed as –log molar $EC_{50}$.

$NK_1$ and $NK_2$ In Vivo Functional Assay (Test E)

The activity of a compound as an antagonist of NK1 and/or NK2 receptors also may be demonstrated in vivo in laboratory animals as described in: Buckner et al. "Differential Blockade by Tachykinin NK1 and NK2 Receptor Antagonists of Bronchoconstriction Induced by Direct-Acting Agonists and the Indirect-Acting Mimetics Capsaicin, Serotonin and 2-Methyl-Serotonin in the Anesthetized Guinea Pig." J. Pharm. Exp. Ther., 1993, Vol 267(3), pp 1168–1175. The assay is carried out as follows.

Compounds are tested in anesthetized guinea pigs pretreated with i.v. indomethacin (10 mg/kg, 20 min.), propranolol (0.5 mg/kg, 15 min.), and thiorphan (10 mg/kg, 10 min).

Antagonists or vehicle are administered i.v. and orally, 30 and 120 minutes prior to increasing concentrations of agonist, respectively. The agonists used in these studies are ASMSP (Ac-[Arg$^6$,Sar$^9$,Met($O_2$)$^{11}$]-SP(6-11)) and BANK (β-ala-8 NKA4-10).

Administered i.v., ASMSP is selective for $NK_1$ receptors, and BANK is selective for $NK_2$ receptors. Maximum response is defined as zero conductance ($G_L$, 1/Rp). $ED_{50}$ values are calculated (the dose of agonist resulting in a reduction of $G_L$ to 50% of baseline), and converted to the negative logarithm (–$logED_{50}$). The $ED_{50}$ values, obtained in the presence (P) and absence (A) of antagonist, are used to calculate a Dose Ratio (P/A), an expression of potency. Data are expressed as mean±SEM and statistical differences were determined using ANOVA/Tukey-Kramer and Student's t-test , with p<0.05 considered statistically significant.

Compounds of the present invention exhibit marked activity in the foregoing tests and are considered useful for the treatment of those diseases in which the NK1 and/or NK2 receptor is implicated, for example, in the treatment of asthma and related conditions.

Results of testing of representative compounds of the present invention by the above methods are presented in the Table I

TABLE 1

| Exam-ple | Rabbit Pulmonary Artery | | Oral Activity (Test E) | |
|---|---|---|---|---|
| | NK1 pKb [% inhibition] (Test C) | NK2 pKb (Test D) | NK1 P/A | NK2 P/A |
| 5 | NA [74% at $10^{-8}$ M] | 7.1 | 454 | ND |
| 6 | 8.3 | 7.6 | 147 | ND |

NA = not applicable,
ND = not determined

Clinical Studies

Clinical studies to demonstrate the efficacy of a Compound of the invention may be carried out using standard methods. For example, the ability of a Compound to prevent or treat the symptoms of asthma or asthma-like conditions may be demonstrated using a challenge of inhaled cold air or allergen and evaluation by standard pulmonary measurements such as, for example, $FEV_1$ (forced expiratory volume in one second) and FVC (forced vital capacity), analyzed by standard methods of statistical analysis.

It will be appreciated that the implications of a Compound's activity in the above described Tests is not limited to asthma, but rather, that the Tests provide evidence of general antagonism of both SP and NKA. SP and NKA have been implicated in the pathology of numerous diseases including: rheumatoid arthritis, Alzheimer's disease, cancer, schizophrenia, oedema, allergic rhinitis, inflammation, pain, gastrointestinal-hypermotility, gastric asthma, gastroesphageal reflux, anxiety, emesis, Huntington's Disease, psychoses including depression, hypertension, migraine, bladder hypermotility and urticaria.

Accordingly, one feature of the invention is the use of a compound of formula I or a pharmaceutically acceptable salt thereof in the treatment of a disease in a human or other mammal in need thereof in which SP or NKA is implicated and antagonism of its action is desired.

Asthma is characterized by both chronic inflammation and hyperresponsiveness of the airways. The NK1 receptor is known to mediate inflammation and mucus hypersecretion in airways; and the NK2 receptor is involved in the control of the tone of bronchial smooth muscle. Thus, agents capable of antagonizing the actions of SP and NKA, at the NK1 and NK2 receptors, respectively, are capable of reducing both the chronic inflammation and the airway hyperresponsiveness which are symptomatic of asthma. It has been suggested that an antagonist having mixed affinity for NK1 and NK2 could be therapeutically superior to a receptor selective antagonist. C. M. Maggi "Tachykinin Receptors and Airway Pathophysiology" *Eur. Respir. J.*, 1993, 6, 735–742 at 739. Also, it has been suggested that a synergistic effect against bronchoconstriction may result from the simultaneous application of an NK1 antagonist and an NK2 antagonist. D. M. Foulon, et al. "NK1 and NK2 Receptors Mediated Tachykinin and Resiniferatoxin-induced Bronchospasm in Guinea Pigs" *American Review of Respiratory Disease*, 1993, 148, 915–921. Accordingly, another feature of the invention is the use of a compound of formula I or a pharmaceutically acceptable salt thereof in the treatment of asthma in a human or other mammal in need thereof. There is a possible role for Substance P antagonists in the treatment of depression. Accordingly another feature of the invention is the use of a compound of formula (I) or a pharmaceutically acceptable salt thereof in the treatment of depression in a human or other mammal in need thereof.

Because of the range of effects attributable to the actions of SP and NKA, compounds which are capable of blocking their actions may also be useful as tools for further evaluating the biological actions of other neurotransmitters in the Tachykinin family. As a result, another feature of the invention is provided by the use of a compound of Formula I or a salt thereof as a pharmacological standard for the development and standardization of new disease models or assays for use in developing new therapeutic agents for treating diseases in which SP or NKA are implicated or for assays for their diagnosis.

The invention is illustrated by the following non-limiting examples, in which, unless stated otherwise:

(i) operations were carried out at room or ambient temperature, that is, at a temperature in the range of 18–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) melting points are uncorrected;

(iv) final products had satisfactory proton nuclear magnetic resonance (NMR) spectra; (v) Mass spectra (MS) were run using an automated system with atmospheric pressure chemical ionization (APCI). Where indicated, the following alternative methods of ionization were used; a) desorption chemical ionization (CI) using methane reagent gas and a direct exposure probe; b) electron impact (EI) or c) fast atom bombardment (FAB). Generally, only spectra where parent masses are observed are reported.

Abbreviations: CO, carbon monoxide; DCM; methylene chloride, DMF; N;N-dimethylformamide, DMSO; dimethyl sulfoxide, $Et_2O$; diethyl ether, EtOAc; ethyl acetate, h; hour(s), min; minutes, NMR; nuclear magnetic resonance, psi; pounds per square inch, THF; tetrahydrofuran.

Standard acylation refers to the typical procedure in which an acid chloride (1–1.2 equivalents) is added to a stirred solution of an amine (1–1.2 equivalents) and triethylamine (2 equivalents) in DCM. After 1–16 h the reaction is optionally concentrated, dissolved in DCM, and washed with saturated sodium bicarbonate and then purified by chromatography.

Standard reductive amination refers to the typical procedure in which a solution of an amine (1–1.2 equivalents), an aldehyde (1–1.2 equivalents) and acetic acid (2 equivalents) are stirred in methanol for 5 to 60 minutes before adding $NaBH_3CN$ (1.7 equivalents). After 1–16 h the reaction is optionally concentrated, dissolved in DCM, and washed with saturated sodium bicarbonate and then purified by chromatography.

Final compounds were converted to the citrate salt. The free base was combined with citric acid (1.0 equivalents) in methanol, concentrated under reduced pressure and dried under vacuum (25–50° C.).

EXAMPLE 1

N-[(S)-2-(3,4-Dichlorophenyl)-4-[4-[(S)-2-methylsulfinylphenyl]-1-Piperidinyl]butyl]-N-methyl-5,6,7,8-tetrahydro-1-naphthamide Using standard acylation conditions N-[(S)-2-(3,4-dichlorophenyl)-4-[4-[(S)-2-methylsulfinylphenyl]-1- piperidinyl]butyl]-N-methylamine was reacted with 5,6,7,8-tetrahydro-1-naphthalenecarbonyl chloride and the product was converted to the citrate salt MS: m/z 611 (M+H). Analysis for $C_{34}H_{40}Cl_2N_2O_2S \cdot C_6H_8O_7 \cdot 0.5\ H_2O$: calculated; C, 58.78; H, 6.11; N, 3.43; found: C, 58.56; H, 6.10; N, 3.32.

The requisite N-[(S)-2-(3,4-dichlorophenyl)-4-[4-[(S)-2-methylsulfinylphenyl]-1-piperidinyl]butyl]-N-methylamine was prepared as follows.

(a) N-[(S)-2-(3,4-Dichlorophenyl)4-[4-[(S)-2-methylsulfinylphenyl]-1-piperidinyl]butyl]-N-methyl-N-Boc-arine.

(S)-N-[2-(3,4-Dichlorophenyl)-4-oxobutyl]-N-methyl-N-Boc-amine (Miller, S C; WO 9505377) (51.7 g, 149.3 mmol), 4-[(S)-2-methylsulfinylphenyl]-piperidine (Shenvi, A B; Jacobs, R T; Miller, S C; Ohnmacht, C J, Jr.; Veale, C A., WO 9516682) (36.7 g, 164.3 mmol), and glacial acetic acid (9.9 g, 165.0 mmol) were dissolved in methanol (1000 mL), and the solution stirred for 15 min. Sodium cyanoborohydride (10.4 g, 165.5 mmol) was added in portions as a solid over 30 min. The mixture was stirred for 20 h, then treated with saturated sodium bicarbonate (500 mL). Methanol was removed in vacuo, and the aqueous residue was extracted with DCM (4×400 mL). The organic layer was washed with brine (300 mL), dried ($MgSO_4$), filtered, and concentrated in vacuo. The residue was purified by chromatography (0–6% methanol in DCM) to provide a white foam (77.2 g, 93%). MS: 553 (M+H). $^1$H-NMR ($CDCl_3$) δ 1.40 (s, 9H, t-$C_4H_9$); 1.61–2.04 (m, 9H, CH); 2.14–2.23 (m, 6H, $NCH_3$, $SOCH3$); 2.91–3.00 (m, 3H, CH); 3.27–3.54 (m, 2H, CH); 7.00–7.09 (m, 1H, aromatic); 7.21–7.53 (m, 5H, aromatic); 7.95–8.04 (m, 1H, aromatic).

(b) N-[(S)-2-(3,4-Dichlorophenyl)-4-[4-[(S)-2-methylsulfinylphenyl]-1-piperidinyl]butyl]-N-methylamine.

N-[(S)-2-(3,4-Dichlorophenyl)-4-[4-[(S)-2-methylsulfinylphenyl]-1-piperidinyl]butyl]-N-methylamine-N-Boc-amine (77.0 g, 139.0 mmol) was dissolved in DCM (1200 mL). To the stirred solution was added trifluoroacetic acid (160.0 g, 1.40 mol) dropwise over 15 min. The mixture was stirred for 4 h, then additional trifluoroacetic acid (80.0 g, 0.70 mol) was added, and the mixture stirred an additional 1.5 h. The mixture was washed with aqueous sodium carbonate (225 g, 1500 mL water), water (2×500 mL), then dried ($MgSO_4$). Filtration and concentration left the crude product as a yellow gum. Purification by chromatography (0–20% methanol/DCM) provided a light yellow foam (61.8 g, 98%). MS: 453 (M+H). $^1$H-NMR ($CDCl_3$) δ 1.64–2.09 (m, 7H, CH); 2.27–2.35 (m, 2H, CH); 2.46 (s, 3H, $NCH_3$); 2.68 (s, 3H, $SOCH_3$); 2.74–3.05 (m, 7H, CH); 3.39–3.78 (bs, 1H, NH); 7.07–7.10 m, 1H, aromatic); 7.23–7.50 (m, 5H, aromatic); 7.95–7.99 (m, 1H, aromatic).

The requisite 5,6,7,8-tetrahydro-1-naphthalenecarbonyl chloride was prepared as follows.

A solution of 5,6,7,8-tetrahydro-1-naphthalenecarboxylic acid (J. W, Burnham, W. P. Duncan, E. J. Eisenbaum, G. W. Keen, M. C. Hamming, Org. Prep. Proc. Int. 285–290 (1973))(0.205 g, 1.16 mmol) in thionyl chloride (3.26 g, 27.42 minol) was heated at 80 ° C. for 3 h under a stream of nitrogen. Excess thionyl chloride was removed in vacuo, and the residue concentrated a second time from toluene to afford 5,6,7,8 tetrahydo-1-naphthalenecarbonyl chloride as a brown oil. The residue was dissolved in dry $CH_2Cl_2$ and used without further purification.

EXAMPLE 2

N-[(S)-2-(3,4-Dichlorophenyl)-4-[4-[tetrahydro-2-oxo-1(2H)-pyrimidinyl]-1-piperidinyl]butyl]-N-methyl-5,6,7,8-tetrahydro-1-naphthamide Using standard acylation conditions N-[(S)-2-(3,4-dichlorophenyl)4-[4-[tetrahydro-2-oxo-1(2H)-pyrimidinyl]-1-piperidinyl]butyl]-N-methylamine (S. C. Miller,. WO 9505377) was reacted with 5,6,7,8-tetrahydro-1-naphthalenecarbonyl chloride (Example 1) and the product was converted to the citrate salt MS: m/z 571 (M+H). Analysis for $C_{31}H_{40}O_2Cl_2N_4 \cdot C_6H_8O_7 \cdot 3.0H_2O$: calculated: C,54.34; H, 6.66; N, 6.85; found: C, 54.26; H, 5.97; N, 6.47.

EXAMPLE 3

N-[(S)-2-(3,4-Dichlorophenyl)-4-[4-[(S)-2-methylsulfinylphenyl]-1-piperidinyl]butyl]-N-methyl-3-nitro-5,6,7,8-tetrahydro-1-naphthamide 3-Nitro-5,6,7,8-tetrahydro-1-naphthalenecarbonyl chloride [from 3-nitro-5,6,7,8-tetrahydro-1-naphthalenecarboxylic acid (0.150 g, 6.78 mmol) and $PCl_5$ (0.190 g, 8.48 mmol) in EtOAc (1.5 mL) as described in T. Nakayama, T. Okutome, R. Matsui, M. Kurumi, Y. Sakurai, T. Aoyama, S. Fujii, Chem. Pharm. Bull. 32(10) 3968 (1984)] was dissolved in EtOAc (2 mL) and added to a stirred solution of N-[(S)-2-(3,4-dichlorophenyl)-4-[4-[(S)-2-methylsulfinylphenyl]-1-piperidinyl]butyl]-N-methylamine (0.3075 g, 0.678 mmol), triethylamine (0.124 mL, 0.892 mmol) and EtOAc (3.1 mL) and the mixture stirred overnight at ambient temperature. The reaction mixture was washed with 10% aqueous HCl, 5% aqueous NaOH and brine solutions, dried ($MgSO_4$) and the solvent removed in vacuo to yield the title compound (0.168 g, 38%) which was converted to the citrate salt MS: m/z 656 (M+H). Analysis for $C_{34}H_{39}Cl_2N_3O_4S \cdot C_6H_8O_7 \cdot 2.0H_2O$: calculated: C, 54.30; H, 5.81; N, 4.75; found: C, 54.10; H, 5.55; N, 4.55.

EXAMPLE 4

N-[(S)-2-(3,4-Dichlorophenyl)4-[4-[(S)-2-methylsulfinylphenyl]-1-piperidinyl]butyl]-N-methyl-4-nitro-5,6,7,8-tetrahydro-1-naphthamide Using a procedure analogous to that described in Example 3, N-[(S)-2-(3,4-dichlorophenyl)4-[4-[(S)-2-methylsulfinylphenyl]-1-piperidinyl]butyl]-N-methylamine was reacted with 4-nitro-5,6,7,8-tetrahydro-1-naphthalenecarbonyl chloride [prepared from 4-nitro-5,6,7,8-tetrahydro-1-naphthalenecarboxylic acid (T. Nakayama, T. Okutome, R. Matsui, M. Kurumi, Y. Sakurai, T. Aoyama, S. Fujii, Chem. Pharm. Bull. 32(10) 3968 (1984))] and the product was converted to the citrate salt MS: m/z 656 (M+H). Analysis for $C_{34}H_{39}Cl_2N_3O_4S \cdot C_6H_8O_7 \cdot 1.0H_2O$: calculated: C, 54.42; H, 5.70; N, 4.85. found: C, 55.03; H, 5.55; N, 4.94.

EXAMPLE 5

N-[(S)-2-(3,4-Dichlorophenyl)-4-[4-[(S)-2-methylsulfinylphenyl]-1-piperidinyl]butyl]-N-methyl-3-cyano-2-methoxy-5,6,7,8-tetrahydro-1-naphthamide Using standard acylation conditions N-[(S)-2-(3,4-dichlorophenyl)-4-[4-[(S)-2-methylsulfinylphenyl]-1-piperidinyl]butyl]-N-methylamine was reacted with 3-cyano-2-methoxy-5,6,7,8-tetrahydro-1-naphthalenecarbonyl chloride and the product was converted to the citrate salt MS: m/z 666 (M+H). Analysis for $C_{36}H_{41}Cl_2N_3O_3S \cdot C_6H_8O_7 \cdot 1.3H_2O$: calculated: C, 57.18; H, 5.90; N, 4.76; found: C, 56.93; H, 5.67; N, 4.74.

The requisite 3-cyano-2-methoxy-5,6,7,8-tetrahydro-1-naphthalenecarbonyl chloride was prepared as follows (a) 3-Hydroxy-5,6,7,8-tetrahydro-2-naphthalenecarboxylic acid A mixture of 3-hydroxy-2-naphthalenecarboxylic acid (15.0 g, 0.08 moles), 10% Pd/C (4.46 g) and acetic acid (190 mL) was hydrogenated at 60° C. and 50 psi for 7 h. The cooled reaction mixture was filtered through diatomaceous earth and washed with ethanol (4×25 mL). The yellow filtrate was concentrated in vacuo to afford 13.82 g (91%) of a purple solid. $^1$H NMR (CDCl$_3$) δ 7.61 (s, 1H), 6.71 (s, 1H), 2.74 (d, 4H), 1,78 (s, 4H). MS m/z 191 (M−H).

(b) 4-Iodo-3-hydroxy-5,6,7,8-tetrahydro-2-naphthalenecarboxylic acid.

Sodium iodide (10.78 g, 0.719 moles) was added to a solution of sodium hydroxide (5.75 g, 0.144 moles) in methanol (100 mL) followed by the addition of 3-hydroxy-5,6,7,8-tetrahydro-2-naphthalenecarboxylic acid (13.82 g, 0.719 moles) and the mixture stirred for 30 min. The resulting suspension was cooled to 0° C. and a 5.25% w/v aqueous solution of sodium hypochlorite (102 g) was added dropwise. After all the hypochlorite solution was added, stirring was continued at 0° C. for 1 h, saturated sodium thiosulfate (70 mL) was added and the solution was allowed to stir for 5 min. 6N HCl was added dropwise until pH 2 was obtained. A whitish-brown precipitate formed. The cold suspension was filtered through a fritted glass funnel and the filter cake was washed with 50 mL of water. The filter cake was transferred to a round-bottomed flask and dissolved in 70 mL of methanol and 100 mL of toluene. The solvents were removed in vacuo to afford a light brown solid (23.43 g, 100%). $^1$H NMR (DMSO) δ 7.53 (s, 1H), 2.63 (m, 4H), 1.70 (m, 4H). MS m/z 317 (M−H).

(c) Methyl 4-iodo-3-methoxy-5,6,7,8-tetrahydro-2-naphthalenecarboxylate

To a stirred suspension of 4-iodo-3-hydroxy-5,6,7,8-tetrahydro-2-naphthalenecarboxylic acid (23.43 g, 73.65 mmol) in dry acetone (450 mL) was added dimethyl sulfate (17.42 mL, 184.13 mmol) and K$_2$CO$_3$ (25.45 g, 184.13 mmol). The mixture was stirred at reflux overnight, cooled and triethylamine (40 mL) was added. After 0.5 h the mixture was filtered through a pad of diatomaceous earth and the filtrate concentrated in vacuo. The residue was dissolved in ethyl acetate (50 mL) and washed successively with 1N HCl (2×50 mL), sat. aqueous sodium bicarbonate (2×50 mL) and brine (50 mL ), dried (Na$_2$SO$_4$), filtered and concentrated in vacuo to afford a brown oil (22.52 g, 90%). $^1$H NMR (CDCl$_3$) δ 7.56 (s, 1H), 3.92 (s, 3H), 3.85 (s, 3H), 2.69 (m, 4H), 1.79 (m, 4H). MS m/z 347 (M+H).

(d) 4-Iodo-3-methoxy-5,6,7,8-tetrahydro-2-naphthalenecarboxylic acid

To a stirred solution of methyl 4-iodo-3-methoxy-5,6,7, 8-tetrahydro-2-naphthalenecarboxylate (3.0 g, 8.67 mmol) in THF (12 mL) and H$_2$O (4 mL) was added 10N NaOH (9 mL). Methanol was added dropwise until the cloudy solution became clear. After stirring overnight at room temperature, the THF was removed in vacuo. The aqueous solution was acidified to pH 2 with 1N HCl and resulting white precipitate was extracted with DCM (3×25 mL). The combined organic extracts were dried (Na$_2$SO$_4$), filtered and concentrated in vacuo to afford a light brown solid (2.8 g, 100%). $^1$H NMR (CDCl$_3$) δ 7.83 (s, 1H), 3.92 (s, 3H), 2.77 (m, 4H), 1.78 (m, 4H). MS m/z 331 (M−H).

(e) 4-Iodo-3-methoxy-5,6,7,8-tetrahydro-2-naphthalenecarboxamide

Thionyl chloride (1.59 mL, 21.80 mmol) was added dropwise over 5 min to a stirred suspension of 4-iodo-3-methoxy-5,6,7,8-tetrahydro-2-naphthalenecarboxylic acid (2.9 g, 8.73 mmol) in toluene (10 mL) and DMF (0.25 mL) at room temperature. After heating at reflux for 3.5 h, the reaction was cooled to 0° C. and added to cooled (0° C.) 28% NH$_4$OH (25 mL). The mixture was stirred at 0° C. for 10 min and at room temperature overnight. The mixture was filtered and the collected solid was thoroughly washed with H$_2$O. The light brown solid (2.07 g, 72%) was dried under high vacuum at 50° C. 1H NMR (CDCl$_3$) δ 7.79 (s, 1H), 7.61 (s, 1H), 5.90 (s, 1H), 3.84 (s, 3H), 2.76 (m, 4H), 1.79 (m, 4H). MS m/z 332 (M+H).

(f) 3-Cyano-2-methoxy-5,6,7,8-tetrahydro-1-iodonaphthalene

To a stirred, cooled (0° C.) suspension of 4-iodo-3-methoxy-5,6,7,8-tetrahydro-2-naphthalenecarboxamide (2.06 g, 6.22 mmol), triethylamine (2.77 mL, 19.91 mmol), and THF (40 mL) was added trifluoroacetic anhydride (1.23 mL, 8.71 mmol) dropwise via syringe. After addition, the ice bath was removed and the reaction stirred overnight at ambient temperature. The mixture was cooled to 0° C. and excess trifluoroacetic anhydride destroyed with H$_2$O (2 mL). Ethyl acetate (50 mL) was added and the organic layer was washed with H$_2$O (3×25 mL) and brine (25 mL), dried (NaSO$_4$), filtered, concentrated in vacuo and purified by chromatography (100% DCM) to afford a light brown solid (1.96 g, 100%). $^1$H NMR (CDCl$_3$) δ 7.29 (s, 1H), 4.0 (s, 3H), 2.74 (m, 4H), 1.76 (m, 4H), MS m/z 314 (M+H).

(g) Methyl 3-cyano-2-methoxy-5,6,7,8-tetrahydro-1-naphthalenecarboxylate

A mixture of 3-cyano-2-methoxy-5,6,7,8-tetrahydro-1-iodonaphthalene (1.96 g, 6.27 mmol), Pd(OAc)$_2$ (70.4 mg, 0.314 mmol), triethylamine (2.18 mL, 15.68 mmol) and methanol (30 mL) was purged with CO for 25 min. The mixture was then heated at 70° C. under an atmosphere of CO (balloon pressure) for 18 h. The solution was cooled and the remaining CO pressure relieved. The solution was filtered through a pad of diatomaceous earth and the pad was rinsed with methanol (20 mL) and CH$_2$Cl$_2$ (20 mL). The filtrate was concentrated in vacuo and purified by chromatography (0–2% ethyl acetate in hexane) to afford the title compound as a white solid (0.65 g, 42%). $^1$H NMR (DMSO) δ 7.34 (s, 1H), 4.01 (s, 3H), 3.93 (s, 3H), 2.72 (m, 4H), 1.78 (m, 4H). MS m/z 246 (M+H).

(h) 3-Cyano-2-methoxy-5,6,7,8-tetrahydro-1-naphthalenecarboxylic acid

To a stirred solution of methyl 3-cyano-2-methoxy-5,6,7, 8-tetrahydro-1-naphthalenecarboxylate (0.65 g, 2.64 mmol) in THF (12 mL) and H$_2$O (4 mL) was added 1N NaOH (3 mL). Methanol was added dropwise until the cloudy solution became clear. After stirring for 96 h at room temperature, the reaction was treated with sat. aqueous sodium bicarbonate and Et$_2$O. The collected aqueous layer was acidified to pH 2 with 1N HCl, the resulting precipitate extracted with DCM (3×25 mL), dried (Na$_2$SO$_4$), filtered and concentrated to afford a white solid (0.115 g, 19%). $^1$H NMR (CDCl$_3$) δ 7.39 (s, 1H), 4.09 (s, 3H), 2.82 (m, 4H), 1.80 (m, 4H).

(i) 3-Cyano-2-methoxy-5,6,7,8-tetrahydro-1-naphthalenecarbonyl chloride

A stirred mixture of 3-cyano-2-methoxy-5,6,7,8-tetrahydro-1-naphthalenecarboxylic acid (0.110 g, 0.476 mmol) and dry CH$_2$Cl$_2$ (2 mL) was treated with oxalyl chloride (51.9 μl) and dry N,N-dimethylformanide (~5 μL) at ambient temperature. After 2.0 h, the solvent was evaporated in vacuo. The residue was dissolved in dry CH$_2$Cl$_2$ and used without further purification.

EXAMPLE 6

N-[2-(S)-(3,4-Dichlorophenyl)4-[-4-[(S)-2-(methylsulfinyl)phenyl]-1-piperidinyl]butyl]-N-methyl-3-cyano-5,6,7.8-tetrahydro-1-naphthamide Using standard acylation conditions 2-(S)-(3,4-dichlorophenyl)-N-methyl-4-[((S)-2-methylsulfinylphenyl)-

1-piperidinyl]butanamine was reacted with 3-cyano-5,6,7,8-tetrahydro-1-naphthalenecarbonyl chloride and converted to the citrate salt. MS m/z 636.3 (M+H); analysis for $C_{35}H_{39}Cl_2N_3O_2S \cdot 1.0 \; C_6H_8O_7 \cdot 1.0 \; H_2O$; calculated: C, 58.15; H, 5.83; N, 4.96; found: C, 58.18; H, 5.69; N, 4.90.

The requisite 3-cyano-5,6,7,8-tetrahydro-1-naphthalenecarbonyl chloride was prepared as follows:

(a) 3-Hydroxy-1-naphthalenecarboxylic acid

Methyl 3-methoxy-1-naphthalenecarboxylate (Bin Ye and Terrence R. Burke, Tetrahedron, 52, 9963–9970 (1996)) (8.13 g, 37.6 mmol) and pyridinium hydrochloride (217 g, 1.88 mol) was heated to 200° C. for 30 min. After cooling to room temperature, 1N HCl was added and the precipitate was filtered and washed with water to give the title compound (6.67 g, 94%) as a yellow solid. 1H-NMR (DMSO-$d_6$): 13.16 (s, 1H), 10.03 (s, 1H), 8.73 (d, 1H), 7.78 (d, 1H), 7.72 (d, 1H), 7.37 (m, 3H); MS m/z 187 (M–H).

(b) Methyl 3-hydroxy-1-naphthalenecarboxylate

To a stirred solution of 3-hydroxy-1-naphthalenecarboxylic acid (6.67 g, 35.4 mmol) and oxalyl chloride (3.86 mL, 44.2 mmol) in DCM (150 mL) was added 3 drops of DMF. The mixture was stirred at room temperature for 3 h., the solvent was removed under reduced pressure and methanol (150 mL) was added. After stirring at reflux for 15 min the solvent was removed under reduced pressure, the residue was purified by column chromatography (10%, 20% and 30% EtOAc/hexane) to give the title compound as a yellow solid (2.5 g, 35%). $^1$H NMR (DMSO-$d_6$) δ 10.10 (s, 1H), 8.61 (d, 1H), 7.77 (d, 1H), 7.72 (d, 1H), 7.47 (m, 2H), 7.38 (d, 1H), 3.93 (s, 3H); MS m/z 201.1 (M–H).

c) Methyl 3-hydroxy-5,6,7,8-tetrahydro-1-naphthalenecarboxylate

A mixture of methyl 3-hydroxy-1-naphthalenecarboxylate (5.77 g, 28.5 mmol) and 10% Pd/C (1.57 g) in HOAc (140 mL) was hydrogenated on a Parr apparatus at 60° C., and 50 psi for 21 h. After filtration through a pad of diatomaceous earth the solvent was removed in vacuo and the residue treated with water and extracted with EtOAc (3×50 mL). The combined organic layers were washed with water, dried (MgSO$_4$) and concentrated to yield product as a yellow oil (5.24 g, 89%). $^1$H NMR (CDCl$_3$) δ 7.20 (d, 1H), 6.73 (d, 1H), 3.86 (s, 3H), 2.94 (d, 2H), 2.76 (d, 2H), 1.74 (m, 4H); MS m/z 205 (M–H).

(d) Methyl 3-trifluoromethylsulfonyloxy-5,6,7,8-tetrahydro-1-naphthalenecarboxylate To a stirred cooled (0° C.) solution of methyl 3-hydroxy-5,6,7,8-tetrahydro-1-naphthalenecarboxylate (2.0 g, 9.7 mmol) in DCM (50 mL) was added triethylamine (1.5 mL, 10.7 mmol) and trifluoromethanesulfonic anhydride (1.8 mL, 10.7 mmol). After stirring at room temperature for 30 min, saturated NaHCO$_3$ was added and the mixture was extracted with DCM. The organic layer was dried (MgSO$_4$), filtered and concentrated. The residue was purified by column chromatography (5% EtOAc/hexane) to give product as a colorless oil (2.16 g, 66%). $^1$H NMR (CDCl$_3$) δ 7.57 (d, 1H), 7.13 (d, 1H), 3.90 (s, 3H), 3.06 (m, 2H), 2.85 (m, 2H), 1.81 (m, 4H).

(e) Methyl 3-cyano-5,6,7,8-tetrahydro-1-naphthalenecarboxylate

A solution of methyl 3-trifluoromethylsulfonyloxy-5,6,7,8-tetrahydro-1-naphthalenecarboxylate (2.08 g, 6.15 mmol), zinc cyanide (0.81 g, 6.89 mmol) and tetrakistriphenylphosphine palladium (0.56 g, 0.48 mmol) in DMF (8 mL) was stirred at 120° C. for 1 h. The mixture was diluted with saturated NaHCO$_3$, extracted with EtOAc, dried (MgSO$_4$), filtered, and concentrated. Following column chromatography methyl-3-cyano-5,6,7,8-tetrahydro-1-naphthalenecarboxylate was obtained as a white solid (960 mg, 73%). $^1$H NMR (CDCl$_3$) δ 7.94 (s, 1H), 7.49 (s, 1H), 3.90 (s, 3H), 3.11 (s, 2H), 2.84 (s, 2H), 1.81 (m, 4H); MS m/z 216.1 (M+H), 214.1 (M–H).

(f) 3-Cyano-5,6,7,8-tetrahydro-1-naphthalenecarboxylic acid

A solution of methyl 3-cyano-5,6,7,8-tetrahydro-1-naphthalenecarboxylate (0.96 g, 4.46 mmol) in THF (54 mL), water (21 mL) and 1N NaOH (9.4 mL, 9.4 mmol) was stirred overnight at room temperature. The THF was removed in vacuo and the mixture acidified to pH 1 with 1N HCl. The resulting precipitate was extracted with EtOAc, dried (MgSO$_4$), filtered and concentrated to give the title compound as a white solid (0.88 g, 98%). $^1$H NMR (DMSO) δ 13.33 (s, 1H), 7.96 (d, 1H), 7.29 (d, 1H), 3.99 (d, 2H), 2.81 (d, 2H), 1.72 (m, 4H); MS m/z 200.1 (M–H).

(g) 3-Cyano-5,6,7,8-tetrahydro-1-naphthalenecarbonyl chloride

To a solution of 3-cyano-5,6,7,8-tetrahydro-1-naphthalenecarboxylic acid (0.207 g, 1.03 mmol) in DCM (5 mL) was added oxalyl chloride (0.112 mL, 1.29 mmol) and 1 drop of DMF. The mixture was stirred at room temperature for 2 h., the solvent was removed in vacuo and the 3-cyano-5,6,7,8-tetrahydro-1-naphthalenecarbonyl chloride was used without purification.

EXAMPLE 7

N-[2-(S)-(3,4-Dichlorophenyl)-4-[4-[(S)-2-(methylsulfinyl)phenyl]-1-piperidinyl]butyl]-N-methyl-3-methoxy-5,6,7,8-tetrahydro-1-naphthamide Using standard acylation conditions 2-(S)-(3,4-dichlorophenyl)-N-methyl-4-[((S)-2-methylsulfinylphenyl)-1-piperidinyl]butanamine was reacted with 3-methoxy-5,6,7,8-tetrahydro-1-naphthalenecarbonyl chloride and converted to the citrate salt. MS m/z 641.3 (M+H); analysis for $C_{35}H_{42}Cl_2N_2O_3S \cdot 1.0 \; C_6H_8O_7 \cdot 1.0 \; H_2O$; calculated; C, 57.81; H, 6.15; N, 3.29; found: C, 57.72; H, 6.01; N, 3.35.

The requisite 3-methoxy-5,6,7,8-tetrahydro-1-naphthalenecarbonyl chloride was prepared as follows:

(a) Methyl 3-methoxy-5,6,7,8-tetrahydro-1-naphthalenecarboxylate

To a solution of methyl 3-hydroxy-5,6,7,8-tetrahydro-1-naphthalenecarboxylate (Example 6 subpart (c)) (1.38 g, 6.69 mmol) in DMF (30 mL) was added NaH (0.32 g, 8.0 mmol). After stirring at room temperature for 1 h, dimethylsulfate (0.76 mL, 8.0 mmol) was added, the mixture stirred at room temperature for 1 h and water and Et$_2$O was added. The separated organic layer was washed with brine, water, dried (MgSO$_4$), filtered and concentrated. Following flash chromatography methyl 3-methoxy-5,6,7,8-tetrahydro-1-naphthalenecarboxylate was obtained as a colorless oil (900 mg, 61%). $^1$H NMR (CDCl$_3$) δ 7.21 (d, 1H), 6.78 (d, 1H), 3.87 (s, 3H), 3.80 (s, 3H), 2.97 (s, 2H), 2.79 (s, 2H), 1.76 (m, 4H); MS m/z 221.1 (M+H).

(b) 3-Methoxy-5,6,7,8-tetrahydro-1-naphthalenecarboxylic acid

A solution of methyl 3-methoxy-5,6,7,8-tetrahydro-1-naphthalenecarboxylate (0.90 g, 4.09 mmol) in THF (50 mL), water (20 mL) and 1N NaOH (8.6 mL, 8.6 mmol) was stirred for 3 days at room temperature. The THF was evaporated and the mixture acidified to pH 1 with 1N HCl. The resulting precipitate was extracted with EtOAc, dried (MgSO$_4$), filtered and concentrated to give the acid as a white solid (0.80 g, 95%). $^1$H NMR (DMSO) δ 12.79 (s, 1H), 7.09 (d, 1H), 6.82 (d, 1H), 3.73 (s, 3H), 2.86 (s, 2H), 2.74 (s, 2H), 1.68 (m, 4H); MS m/z 205 (M−H).
(c) 3-Methoxy-5,6,7,8-tetrahydro-1-naphthalenecarbonyl chloride To a solution of 3-methoxy-5,6,7,8-tetrahydro-1-naphthalenecarboxylic acid (0.20 g, 0.97 mmol) in DCM (5 mL) was added oxalyl chloride (0.11 mL, 1.21 mmol) and 1 drop of DMF. The mixture was stirred at room temperature for 2 h. The solvent was removed in vacuo and 3-methoxy-5,6,7,8-tetrahydro-1-naphthalenecarbonyl chloride was used without purification.

EXAMPLE 8

N-[2-(S)-(3,4-Dichlorophenyl)-4-[4-[(S)-2-(methylsulfinyl)phenyl]-1-piperidinyl]butyl]-N-methyl-2-methoxy-5,6,7,8-tetrahydro-1-naphthamide Using standard acylation conditions 2-(S)-(3,4-dichlorophenyl)-N-methyl-4-[((S)-2-methylsulfinylphenyl)-1-piperidinyl]butanamine was reacted with 2-methoxy-5,6,7,8-tetrahydro-1-naphthalenecarbonyl chloride and converted to the citrate salt. MS m/z 641 (M+H); analysis for $C_{35}H_{42}Cl_2N_2O_3S \cdot 1.0\ C_6H_8O_7 \cdot 1.3\ H_2O$; calculated: C, 57.45; H, 6.18; N, 3.27; found: C, 57.43; H, 6.12; N, 3.26.

The requisite 2-methoxy-5,6,7,8-tetrahydro-1-naphthalenecarbonyl chloride was prepared as follows:
(a) 2-Methoxy-5,6,7,8-tetrahydro-1-naphthalenecarboxylic acid A mixture of 2-methoxy-1-naphthalenecarboxylic acid (1.0 g, 4.95 mmol) and 10% Pd/C (0.3 g) in HOAc (25 mL) was hydrogenated on Parr apparatus at 60° C. and 50 psi for 23 h. After filtration through diatomaceous earth, the solvent was removed under reduced pressure, and water was added. The solid was filtered and washed with water to give product as a yellow solid (0.377 g, 37%). $^1$H NMR (DMSO-d$_6$) δ 12.81 (s, 1H), 7.05 (d, 1H), 6.83 (d, 1H), 3.68 (s, 3H), 2.66 (s, 2H), 2.59 (s, 2H), 1.69 (m, 4H); MS m/z 205 (M−H).
(b) 2-Methoxy-5,6,7,8-tetrahydro-1-naphthalenecarbonyl chloride To a solution of 2-methoxy-5,6,7,8-tetrahydro-1-naphthalenecarboxylic acid (0.20 g, 0.97 mmol) in DCM (5 mL) was added oxalyl chloride (0.11 mL, 1.21 mmol) and 1 drop of DMF. The mixture was stirred at room temperature for 2 h. The solvent was removed in vacuo and the 2-methoxy-5,6,7,8-tetrahydro-1-naphthalenecarbonyl chloride was used without purification.

EXAMPLE 9

N-[2-(S)-(3,4-Dichlorophenyl)-4-[4-[(S)-2-(methylsulfinyl)phenyl]-1-piperidinyl]butyl]-N-methyl-3,4-dimethoxy-5,6,7,8-tetrahydro-1-naphthamide Using standard acylation conditions 2-(S)-(3,4-dichlorophenyl)-N-methyl-4-[((S)-2-methylsulfinylphenyl)-1-piperidinyl]butanamine was reacted with 3,4-dimethoxy-5,6,7,8-tetrahydro-1-naphthalenecarbonyl chloride and converted to the citrate salt. MS m/z 671 (M+H); analysis for $C_{36}H_{44}Cl_2N_2O_4S \cdot 1.0\ C_6H_8O_7 \cdot 1.0\ H_2O$; calculated: C, 57.20; H, 6.17; N, 3.18; found: C, 57.18; H, 6.19; N, 3.16.

The requisite 3,4-dimethoxy-5,6,7,8-tetrahydro-1-naphthalenecarbonyl chloride was prepared as follows:
(a) 1,2-Dimethoxynaphthalene To the solution of 1,2-dihydroxynaphthalene (5 g, 31.2 mmol) in DMF (140 mL) was added NaH (3.0 g, 75.0 mmol). After stirred at room temperature for 1 h, dimethylsulfate (7.09 mL, 75.0 mmol) was added. After stirring at room temperature for 22 h, water and Et$_2$O was added, the organic layer was washed with brine, water, dried (MgSO$_4$), filtered and concentrated. Column chromatography yielded the title compound as a colorless oil (3.83 g, 65%). $^1$H NMR (CDCl$_3$) δ 8.12 (d, 1H), 7.79 (d, 1H), 7.59 (d, 1H), 7.47 (m, 1H), 7.35 (m, 1H), 7.29 (d, 1H), 3.99 (s, 3H), 3.99 (s, 3H).
(b) 1-Bromo-3,4-dimethoxynaphthalene To the solution of 1,2-dimethoxynaphthalene (3.83 g, 20.3 mmol) in THF (100 mL) was added dropwise at 0° C. a solution of NBS (3.62 g, 20.3 mmol) in THF (50 mL). After stirring at 0° C. for 0.5 h, the solvent was removed in vacuo and CCl$_4$ was added. The mixture was filtered and the filtrate was concentrated. Column chromatography yielded the title compound as a yellow oil (3.72 g, 68%). $^1$H NMR (CDCl$_3$) δ 8.1 (m, 2H), 7.60 (s, 1H), 7.49 (m, 2H), 3.99 (s, 3H) 3.98 (s, 3H); MS m/z 267 (M−H).
(c) Methyl 3,4-dimethoxy-1-naphthalenecarboxylate A solution of 1-bromo-3,4-dimethoxylnaphthalene (3.72 g, 13.9 mmol), 1,3-bis(diphenylphosphino)propane (0.29 g, 0.7 mmol), palladium acetate (0.16 g, 0.70 mmol), triethylamine (4.85 mL, 34.8 mmol), MeOH (11.5 mL) and DMSO (17 mL) was heated to 75° C. Carbon monoxide was bubbled through the solution for 30 min and the mixture heated under CO (1 atm) for 23 h. The mixture was diluted with brine and extracted with EtOAc (3×70 mL). The organic layers were dried (MgSO$_4$), filtered, and concentrated. Column chromatography gave methyl 3,4-dimethoxy-1-naphthalenecarboxylate as a yellow oil (2.93 g, 85%). $^1$H NMR (CDCl$_3$) δ 8.89 (m, 1H), 8.21 (m, 1H), 8.06 (s, 1H), 7.52 (m, 2H), 4.06 (s, 3H), 4.02 (s, 3H), 4.00 (s, 3H); MS (APCI) m/z 247 (M+H).
(d) 3,4-Dimethoxy-1-naphthalenecarboxylic acid A solution of methyl 3,4-dimethoxyl-1-naphthalenecarboxylate (2.93 g, 11.9 mmol), THF (145 mL), water (58 mL), and 1N NaOH (25 mL, 25.0 mmol) was stirred at room temperature overnight. The THF was removed in vacuo and the mixture acidified to pH 1 with 1N HCl. The resulting white precipitate was extracted with EtOAc (2×50 mL), dried (MgSO$_4$) and filtered to give the product as a white solid (2.55 g, 92%). $^1$H NMR (DMSO) δ 13.19 (s, 1H), 8.89 (d, 1H), 8.13 (d, 1H), 8.08 (s, 1H), 7.54 (m, 2H), 3.97 (s, 3H), 3.98 (s, 3H); MS (APCI) m/z 231 (M−H$^+$).
(e) 3,4-Dimethoxy-5,6,7,8-tetrahydro-1-naphthalenecarboxylic acid A mixture of 3,4-dimethoxy-1-naphthalenecarboxylic acid (2.34 g, 10.1 mmol) and 10% Pd/C (0.56 g) in HOAc (50 mL) was hydrogenated on Parr apparatus at 60° C. and 50 psi for 14 h. After filtration through diatomaceous earth, the solvent was removed in vacuo and water was added. The solid was collected by filtration and washed with water to yield the title compound as a yellow solid (2.21 g, 93%). $^1$H NMR (DMSO-d$_6$) δ 12.69 (s, 1H), 7.30 (s, 1H), 3.79 (s, 3H), 3.73 (s, 3H), 2.91 (s, 2H), 2.65 (s, 2H), 1.64 (m, 4H); MS m/z 235 (M−H).
(f) 3,4-Dimethoxy-5,6,7,8-tetrahydro-1-naphthalenecarbonyl chloride To a solution of 3,4-dimethoxy-5,6,7,8-tetrahydro-1-naphthalenecarboxylic acid (0.20 g, 0.85 mmol) in DCM (5 mL) was added oxalyl chloride (0.09 mL, 1.06 mmol) and 1 drop of DMF. The mixture was stirred at room temperature for 2 h. The solvent was removed in vacuo and the 3,4-dimethoxy-5,6,7,8-tetrahydro-1-naphthalenecarbonyl chloride was used without purification.

EXAMPLE 10

N-[2-(S)-(3,4-Dichlorophenyl)-4-[4-[(S)-2-(methylsulfinyl)phenyl]-1-piperidinyl]butyl]-N-methyl-2,3-dimethoxy-5,6,7,8-tetrahydro-1-naphthamide Using standard acylation conditions 2-(S)-(3,4-dichlorophenyl)-N-methyl-4-[((S)-2-methylsulfinylphenyl)-

1-piperidinyl]butanaamine was reacted with 2,3-dimethoxy-5,6,7,8-tetrahydro-1-naphthalenecarbonyl chloride and converted to the citrate salt. MS m/z 671 (M+H); analysis for $C_{36}H_{44}Cl_2N_2O_4S \cdot C_6H_8O_7 \cdot 0.75$ $H_2O$; calculated: C, 57.50; H, 6.15; N, 3.19; found: C, 57.59; H, 6.02; N, 3.07.

The requisite 2,3-dimethoxy-5,6,7,8-tetrahydro-1-naphthalenecarbonyl chloride was prepared as follows:

(a) 2,3-Dihydroxy-1-naphthaldehyde

A stream of HCl gas was passed through a stirred, cooled (0° C.) mixture of 2,3-dihydroxynaphthalene (6 g, 37.4 mmol) and zinc cyanide (6.6 g, 56.1 mmol) in dry $Et_2O$ (28 mL) for 20 min. An insoluble yellow oil was generated. Stirring was continued for 1 h at 0° C., then at room temperature for 1 h. The yellow brown oil was separated and washed with $Et_2O$. Water (120 mL) was added and the mixture was heated at 60° C. for 10 min. The yellow solid generated was filtered and washed with water to give product (5.48 g, containing 20% starting material). MS (APCI) m/z 187 (M–H).

(b) 2,3-Dimethoxy-1-naphthaldehyde

The impure 2,3-dihydroxy-1-naphthaldehyde (4.87 g, 25.8 mmol), potassium carbonate (14.2 g, 102.9 mmol), and iodomethane (16 mL, 258 mmol) in acetone (80 mL) was heated at 59° C. for 29 h. The solvent was evaporated and the mixture diluted with EtOAc. The organic layer was dried ($MgSO_4$), filtered, and concentrated. Following column chromatography the product was recovered as white solid (3.7 g, 66%). $^1$H NMR (CDCl$_3$) δ 10.82 (s, 1H), 9.10 (d, 1H), 7.71 (d, 1H), 7.51 (m, 2H), 7.43 (s, 1H), 4.06 (s, 3H), 4.03 (s, 3H). MS m/z 217 (M+H).

(c) 2,3-Dimethoxy-1-naphthalenecarboxylic acid.

To a solution of 2,3-dimethoxy-1-naphthaldehyde (3.7 g, 17.1 mmol) in acetone was added sodium carbonate (1.81 g, 17.1 mmol) in water (9 mL), followed by the portionwise addition of potassium permanganate (2.7 g, 17.1 mmol). The mixture was stirred at room temperature for 3 h and filtered. The filtrate was concentrated and extracted with EtOAc. The aqueous layer was acidified to pH 1 with 1N HCl and extracted with EtOAc. The combined organic layers were dried ($MgSO_4$), filtered, and concentrated to give product as a yellow solid (2.41 g, 61%). $^1$H NMR (DMSO) δ 13.46 (s, 1H), 7.86 (d, 1H), 7.63 (d, 1H), 7.51 (s, 1H), 7.42 (m, 2H), 3.96 (s, 3H), 3.83 (s, 3H). MS (APCI) rm/z 231 (M–H).

(d) 2,3-Dimethoxy-5,6,7,8-tetrahydro-1-naphthalenecarboxylic acid

A mixture of 2,3-dimethoxy-1-naphthalenecarboxylic acid (2.21 g, 9.52 mmol) and 10% Pd/C (0.53 g) in HOAc (50 mL) was hydrogenated on a Parr apparatus at 60° C. and 50 psi for 11 h. After filtration through diatomaceous earth, the solvent was removed under reduced pressure, and water was added. The precipitate was filtered and washed with water to give the product as a white solid (1.62 g, 72%). $^1$H NMR (DMSO-d$_6$) δ 12.99 (s, 1H), 6.77 (s,1H), 3.77 (s, 3H), 3.68 (s, 3H), 2.67 (s, 2H), 2.50 (s, 2H), 1.68 (m, 4H); MS m/z 235 (m–H).

(e) 2,3-Dimethoxy-5,6,7,8-tetrahydro-1-naphthalenecarbonyl chloride

To a solution of 2,3-dimethoxy-5,6,7,8-tetrahydro-1-naphthalenecarboxylic acid (0.20 g, 0.85 mmol) in DCM (5 mL) was added oxalyl chloride (0.09 mL, 1.06 mmol) and 1 drop of DMF. The mixture was stirred at room temperature for 2 h. The solvent was removed in vacuo and the 2,3-dimethoxy-5,6,7,8-tetrahydro-1-naphthalenecarbonyl chloride was used without purification.

EXAMPLE 11

N-[2-(S)-(3,4-Dichlorophenyl)-4-[4-[(S)-2-(methylsulfinyl)phenyl]-1-piperidinyl]butyl]-N-methyl-3-isopropoxy-5,6,7.8-tetrahydro-1-naphthamide Using standard acylation conditions 2-(S)-(3,4-dichlorophenyl)-N-methyl-4-[((S)-2-methylsulfinylphenyl)-1-piperidinyl]butanamine was reacted with 3-(isopropoxy)-5,6,7,8-tetrahydro-1-naphthalenecarbonyl chloride and converted to the citrate salt. MS m/z 669 (M+H); analysis for $C_{37}H_{46}Cl_2N_2O_3S \cdot 1.0$ $C_6H_8O_7$ 0.70 $H_2O$; calculated: C, 59.06; H, 6.38; N, 3.20; found: C, 59.06; H, 6.29; N, 3.16.

The requisite 3-(isopropoxy)-5,6,7,8-tetrahydro-1-naphthalenecarbonyl chloride was prepared as follows:

(a) Methyl 3-(isopropoxy)-1-naphthalenecarboxylate

A mixture of methyl 3-hydroxy-1-naphthalenecarboxylate (Example 6 subpart (b)) (0.94 g, 4.65 mmol), potassium carbonate (0.96 g, 6.98 mmol), isopropyl bromide (0.66 mL, 6.98 mmol) and acetone (46 mL) was heated at reflux for 44 h. After filtration the solvent was removed in vacuo. Column chromatography yielded the title compound as a light yellow oil (0.6 g, 53%). $^1$H NMR (CDCl$_3$) δ 8.78 (m, 1H), 7.84 (d, 1H), 7.74 (m, 1H), 7.46 (m, 2H), 7.33 (d, 1H), 4.72 (m, 1H), 3.99 (s, 3H), 1.42 (s, 3H), 1.40 (s, 3H).

(b) 3-(Isopropoxy)-1-naphthalenecarboxylic acid

A solution of methyl 3-isopropoxy)-naphthalenecarboxylate (0.60 g, 2.46 mmol) in THF (30 mL), water (12 mL) and 1N NaOH (5.16 mL, 5.16 mmol) was stirred for 21 h at room temperature. The THF was removed in vacuo and the aqueous solution acidified to pH 1 with 1N HCl. The resulting precipitate was extracted with EtOAc, dried (MgSO$_4$), filtered and concentrated to yield title acid as a white solid (0.53 g, 94% yield). $^1$H NMR (DMSO-d$_6$) δ 13.22 (s, 1H), 8.71 (d, 1H), 7.90 (d, 1H), 7.68 (d, 1H), 7.60 (d, 1H), 7.47 (m, 2H), 4.81 (m, 1H), 1.36 (s, 3H), 1.34 (s, 3H). MS rm/z 229 (M–H).

(c) 3-(Isopropoxy)-5,6,7,8-tetrahydro-1-naphthalenecarboxylic acid

A mixture of 3-(isopropoxy)-1-naphthalenecarboxylic acid (0.38 g, 1.65 mmol) and 10% Pd/C (0.10 g) in HOAc (20 mL) was hydrogenated on Parr apparatus at 60° C. and 50 psi for 13 h. After filtration through diatomaceous earth the solvent was removed in vacuo, water was added and the precipitate was extracted into EtOAc. The combined organic layers were dried (MgSO$_4$), filtered and concentrated to yield the title acid as a light yellow oil (0.39 g, 100%). $^1$H NMR (CDCl$_3$) δ 7.39 (d, 1H), 6.83 (d, 1H), 4.55 (m, 1H), 3.02 (s, 2H), 2.80 (s, 2H), 1.77 (m, 4H), 1.34 (s, 3H), 1.32 (s, 3H); MS m/z 233 (M–H).

(d) 3-(Isopropoxy)-5,6,7,8-tetrahydro-1-naphthalenecarbonyl chloride

To a solution of 3-(isopropoxy)-5,6,7,8-tetrahydro-1-naphthalenecarboxylic acid (0.318 g, 1.36 mmol) in DCM (5 mL) was added oxalyl chloride (0.15 mL, 1.70 mmol) and 2 drops of DMF. The mixture was stirred at room temperature for 3 h. The solvent was removed in vacuo and the 3-(isopropoxy)-5,6,7,8-tetrahydro-1-naphthalenecarbonyl chloride was used without purification.

EXAMPLE 12

N-[2-(3,4-Difluorophenyl)-4-[4-[(S)-2-methylsulfinylphenyl]-1-piperidinyl]butyl]-N-methyl-5,6,7,8-tetrahydro-1-naphthamide Using standard reductive amination conditions N-[2-(3,4-difluorophenyl)-4-oxobutyl]-N-methyl-5,6,7,8-tetrahydro-1-naphthamide was reacted with 4-[(S)-2-methylsulfinylphenyl]piperidine and the product converted to the citrate salt. MS: m/z 579 (M+H). Analysis for $C_{34}H_{40}F_2N_2O_2S \cdot C_6H_8O_7 \cdot 1.9$ $H_2O$: calculated: C, 59.67; H, 6.49; N, 3.48; found: C, 59.30; H, 6.28; N, 4.36.

The requisite N-[2-(3,4-difluorophenyl)4-oxobutyl]-N-methyl-5,6,7,8-tetrahydro-1-naphthamide was prepared as follows:

(a) 2-[[3-Cyano-3-(3,4-difluorophenyl)]propyloxy]-2H-tetrahydropyran.

To a stirred cooled (0° C.) mixture of 60% sodium hydride (4.12 g, 103 mmol) in THF (95 mL) was added dropwise a solution of 3,4-difluorobenzyl cyanide (15.0 g, 98 mmol) in THF (25 mL) and the solution was stirred at room temperature for 3 h. The solution was cooled (ice bath) and 2-(2-bromoethoxy)-2H-tetrahydropyran (20.5 g, 98 mmol) was added dropwise and the solution stirred at room temperature overnight. Saturated ammonium chloride was added and the mixture was extracted with EtOAc. The combined organic extracts were dried (MgSO$_4$), filtered, and concentrated in vacuo. Chromatography (20%, 90% and 95% DCM in hexane) provided the title compound (16.05 g, 58%) as a yellow oil. $^1$H-NMR (CDCl$_3$) δ 1.55–1.63 (m, 4H, CH$_2$) 1.75–1.80 (m, 2H, CH$_2$) 2.10–2.19 (m, 2H, CH$_2$) 3.52–3.58 (m, 2H, CH$_2$) 3.82–4.06 (m, 2H, CH$_2$) 4.08–4.11 (t, 1H, CH) 4.56–4.60 (m, 1H, CH) 7.08–7.27 (m, 3H, ArH).

(b) 2-[[4-Amino-3-(3,4-difluorophenyl)]butyloxy]-2H-tetrahydropyran

To a mixture of Raney Nickel (5.6 g) in ethanol (20 mL) was added 2-[[3-cyano-3-(3,4-difluorophenyl)]propyloxy]-2H-tetrahydropyran (8.34 g, 89.4 mmol) in ethanol (144 mL). Ammonium hydroxide (30%, 120 mL) was added and the mixture was set on Parr apparatus under hydrogen (50 psi) for 4 days. The hydrogenation reaction was combined with a similar reaction (7.70 g, 27.4 mmol of starting nitrile) and filtered through diatomaceous earth. The filtrate was concentrated, DCM and water were added and the layers separated. The organic layer was washed twice with water, dried (Na$_2$SO$_4$), filtered, and concentrated in vacuo to yield 15.40 g (95%) of the title compound as a yellow oil. MS m/z 286 (M+H).

(c) 4-Amino-3-(3,4-difluorophenyl)-1-butanol

To a stirred cooled (5° C.) solution of 2-[[4-amino-3-(3,4-difluorophenyl)]butyloxy]-2H-tetrahydropyran (14.18 g, 49.7 mmol) in methanol (100 mL) was added dropwise 6N HCl (11 mL) and the solution was stirred at room temperature overnight The reaction mixture was poured into water and DCM, and the layers separated. The aqueous phase was basified with 5N NaOH and extracted with DCM. The combined DCM extracts were dried (Na$_2$SO$_4$), filtered, and concentrated in vacuo to provide the title compound as a white solid (8.45 g, 85%). 1H-NMR (300 CDCl$_3$) δ 1.80–1.94 (m, 2H, CH) 2.28 (br s, 3H, NH$_2$, OH) 2.69–2.76 (m, 1H, CH) 2.81–2.88 (dd, 1H, CH) 2.94–2.99 (dd, 1H, CH) 3.49–3.57 (m, 1H, CH) 3.64–3.71 (m, 1H, CH) 6.88–7.18 (m, 3H, ArH). MS m/z 202 (M+H).

(d) 3-(3,4-Difluorophenyl)4-(ethoxycarbonylamino)-1-butanol

Ethyl chloroformate (3.9 mL, 40.8 mmol) was added dropwise to a stirred cooled (−40° C.) solution of 4-amino-3-(3,4-difluorophenyl)-1-butanol (7.45 g, 37 mmol) and triethylamine (5.94 mL, 42.6 mmol) in DCM (180 mL). The solution was stirred at room temperature for 30 min and at room temperature overnight. The material was washed twice with 1N HCl, twice with saturated sodium bicarbonate; dried (Na$_2$SO$_4$), filtered and the solvent removed to provide the title compound (8.85 g, 88%) as a yellow oil. $^1$H-NMR (CDCl$_3$) δ 1.18–1.23 (t, 3H, CH) 1.72–1.98 (m, 3H) 2.96–3.00 (m, 1H, CH) 3.24–3.29 (m, 1H, CH) 3.45–4.04 (m, 3H, CH), 4.06–4.14 (m, 2H, CH) 4.66 (br. s, 1H, OH or NH) 6.91–7.37 (m, 3H, ArH). MS m/z 274 (M+H).

(e) 3(3,4-Difluorophenyl)-N-methyl-4-amino-1-butanol

To a stirred cooled (−10° C.) mixture of lithium aluminum hydride (2.46 g, 65 mmol) and dry THF (50 mL) was added dropwise a solution of 3-(3,4-difluorophenyl)4-(ethoxycarbonylamino)-1-butanol (8.85 g, 32.4 mmol) in THF (40 mL). The solution was heated under reflux for 1.25 h, cooled (ice bath) and saturated sodium sulfate (150 mL) solution was added dropwise. The mixture was stirred at room temperature for 1 hr, filtered through diatomaceous earth, washed with THF and the solvent removed in vacuo. The residue was dissolved in DCM, washed with water, dried (Na$_2$SO$_4$), filtered and the solvent removed in vacuo. Purification by chromatography (2–5% and 10% methanol in DCM) provided the title compound (5.20 g, 75%) as a pale green oil. $^1$H-NMR (CDCl$_3$) δ 1.85–1.96 (m, 2H, CH) 2.45 (s, 3H, CH$_3$) 2.74–2.85 (m, 3H, CH) 3.37 (br s, 2H, NH, OH) 3.50–3.58 (m, 1H, CH) 3.66–3.73, m, 1H, CH), 6.87–7.35 (m, 3H, ArH). MS m/z 216 (M+H).

(f) N-[2-(3,4-Difluorophenyl)-4-hydroxybutyl]-N-methyl-5,6,7,8-tetrahydro-1-naphthamide To a stirred cooled (0° C.) mixture of 3-(3,4-difluorophenyl)-N-methyl-4-amino-1-butanol (0.917 g, 4.26 mmol) in DCM (35 mL) and 1N NaOH (10 mL) was added dropwise a solution of 5,6,7,8-tetrahydro-1-naphthalenecarbonyl chloride (0.829 g, 4.26 mmol) in DCM (20 mL). The mixture was stirred at 0° C. for 2.5 h, additional H$_2$O and DCM were added and the mixture was extracted with DCM (2×20 mL). The combined organic layers were dried (MgSO$_4$), filtered, and concentrated in vacuo. Purification by chromatography (0%, 50%, 100% EtOAc in Et$_2$O) provided the title compound (1.25 g, 79%) as a solid. MS m/z 374 (M+H).

(g) N-[2-(3,4-Difluorophenyl)4-oxobutyl]-N-methyl-5,6,7,8-tetrahydro-1-naphthamide To a stirred cooled (−78° C.) solution of oxalyl chloride (0.546 mL, 6.26 mmol) in DCM (2.55 mL) was added DMSO (0.888 mL, 12.52 mmol) in DCM (3.94). The solution was stirred at −78° C. for 5 min and a solution of N-[$^2$-(3,4-difluorophenyl)-4-hydroxybutyl]-N-methyl-5,6,7,8-tetrahydro-1-naphthamide (1.17 g, 3.13 mmol) in DCM (6.3 mL) and DMSO (3.32 mL) was added dropwise. The solution was stirred at −78° C. for 15 min and triethylamine (2.52 mL, 18.1 mmol) was added. Stirring was continued at −78° C. for 30 min and then at room temperature for 2 h. Additional H$_2$O and DCM (25 mL) were added, the layers separated, and the organic layer was dried (MgSO$_4$), filtered, and concentrated in vacuo. Purification by chromatography (silica gel; Et$_2$O) provided the title compound (1.10 g, 95%) as a brown gum. MS m/z 372 (M+H).

EXAMPLE 13

N-[2-(3,4-Difluorophenyl)-4-[4-[2-methylsulfonylphenyl]-1-piperidinyl]butyl]-N-methyl-5,6,7,8-tetrahydro-1-naphthamide Using standard reductive amination conditions N-[2-(3,4-difluorophenyl)-4-oxobutyl]-N-methyl-5,6,7,8-tetrahydro-1-naphthamide was reacted with 4-[2-methylsulfonylphenyl]piperidine and converted to the citrate salt. MS: m/z 595 (M+H). Analysis for C$_{34}$H$_{40}$F$_2$N$_2$O$_3$S.C$_6$H$_8$O$_7$.1.4 H$_2$O: calculated: C, 59.16; H, 6.31; N, 3.45; found: C, 59.04; H, 6.10; N, 4.08.

EXAMPLE 14

N-[2-(3,4-Difluorophenyl)-4-[4-(tetrahydro-2-oxo-1(2H)-Pyrimidinyl)-4-methylaminocarbonyl)-1-piperidinyl]butyl]-N-methyl-5,6,7,8-tetrahydro 1-naphthamide Using standard reductive amination conditions N-[2-(3,4-difluorophenyl)-4-oxobutyl]-N-methyl-5,6,7,8- tetrahydro-1-naphthamide was reacted with N-(4-[4-(tetrahydro-2-oxo-1($^2$H)-pyrimidinyl)-4-(methylaminocarbonyl)piperidine (Miller, S C; WO 9512577) and converted to the citrate salt. MS: m/z 596 (M+H). Analysis for $C_{33}H_{43}F_2N_5O_3 \cdot 2.0 \ C_6H_8O_7 \cdot 1.5 \ H_2O$: calculated: C, 53.67; H, 6.21; N, 6.96; found: C, 54.29; H, 6.16; N, 7.42.

EXAMPLE 15

N-[2-(4-Chlorophenyl)-4-[4-[(S)-2-methylsufinylphenyl]-1-piperidinyl]butyl]-N-methyl-5,6,7,8-tetrahydro-1-naphthamide Using standard reductive amination conditions N-[2-(4-chlorophenyl)-N-methyl-5,6,7,8-tetrahydro-1-naphthamide was reacted with 4-[(S)-2-methylsulfinylphenyl]piperidine and converted to the citrate salt. MS: m/z 577 (M+H). Analysis for $C_{34}H_{41}ClN_2O_2S \cdot C_6H_8O_7 \cdot 0.9 \ H_2O$: calculated: C, 61.04; H, 6.51; N, 3.55; found: C, 61.20; H, 6.44; N, 3.28.

The requisite N-[2-(4-chlorophenyl)-4-oxobutyl]-N-methyl-5,6,7,8-tetrahydro-1-naphthamide was prepared as follows:

(a) 2-[[3-Cyano-3-(4-chlorophenyl)]propyloxy]-2H-tetrahydropyran

To a stirred cooled (0° C.) mixture of 60% sodium hydride (3.73 g, 93.3 mmol) in THF (80 mL) was added dropwise a solution of 4-chlorobenzylcyanide (13.0 g, 85.8 mmol) in THF (20 mL) and the solution was stirred at room temperature for 3 h. The solution was cooled (ice bath) and 2-(2-bromoethoxy)-2H-tetrahydropyran (15 g, 71.7 mmol) was added dropwise and the solution stirred at room temperature overnight. Saturated ammonium chloride was added and the mixture was extracted with EtOAc. The combined organic extracts were dried (MgSO$_4$), filtered, and concentrated in vacuo. Purification by chromatography (30%, 50%, 60% and 80% DCM in hexane) provided the title compound (19.7 g, 98% yield) as a yellow oil. $^1$H-NMR (CDCl$_3$): δ 1.53–1.64 (m, 4H, CH) 1.71–1.82 (m, 2H, CH) 2.09–2.16 (m, 2H, CH) 3.52–3.57 (m, 2H, CH) 3.80–3.93 (m, 2H, CH) 4.05–4.10 (t, 1H, CH) 4.55–4.60 (m, 1H, CH) 7.28–7.41 (m, 4H, ArH). MS m/z 284 (M+H).

(b) 2-[[4-Amino-3-(4-chlorophenyl)]butyloxy]-2H-tetrahydropyran

To a mixture of Raney Nickel (8.0 g) in ethanol (20 mL) was added a solution of 2-[[3-cyano-3-(4-chlorophenyl)]propyloxy]-2H-tetrahydropyran.(25 g, 89.4 mmol) in ethanol (160 mL). Nitrogen was bubbled through the mixture for 5 min and ammonium hydroxide (30%, 120 mL) was added. The mixture was set on Parr apparatus under hydrogen (50 psi) for 5 days and filtered through diatomaceous earth. The filtrate was concentrated, DCM and water were added and the layers separated. The organic layer was dried (MgSO$_4$), filtered, and concentrated in vacuo. Purification by chromatography (1–5% methanol in DCM) provided the title compound (13.0 g, 51%) as a light yellow oil. $^1$H-NMR (CDCl$_3$): δ 1.51 (m, 4H, CH) 1.65 (m, 1H, CH) 1.74–1.82 (m, 2H, CH) 1.95–2.01 (m, 1H, CH) 2.76–2.97 (m, 3H, CH) 3.16–3.18 (m, 1H, CH) 3.41–3.44 (m, 1H, CH) 3.57–3.80 (m, 2H, CH) 4.41–4.49 (dd, 1H, CH) 7.11–7.16 (m, 2H, ArH) 7.28–7.30 (m, 2H, ArH). MS 284 (M+H).

(c) 4-Amino-3-(4-chlorophenyl)-1-butanol

To a stirred solution of 2-[[4-amino-3-(4-chlorophenyl)]butyloxy]-2H-tetrahydropyran (13.0 g, 45.7 mmol) in methanol (90 mL) was added 6N HCl (11 mL) and the solution was stirred at room temperature overnight. The solvent was removed in vacuo and the residue dissolved in water. The aqueous solution was extracted with Et$_2$O, the pH was adjusted to 14 with 5N sodium hydroxide and the mixture was extracted with EtOAc. The combined EtOAc extracts were washed with saturated sodium chloride solution, dried (MgSO$_4$), filtered and concentrated in vacuo to provide the title compound (9.0 g, 99%). 1H-NMR (CDCl$_3$): δ 1.80–1.96 (m, 2H, CH) 2.53 (s, 3H, OH, NH) 2.71–2.75 (m, 1H, CH) 2.83–3.00 (m, 2H, CH) 3.49–3.57 (m, 1H, CH) 3.63–3.70 (m, 1H, CH) 7.10–7.15 (dd, 2H, ArH) 7.27–7.30 (dd, 2H, ArH). MS m/z 200 (M+H).

(d) 3-(4-Chlorophenyl)-4-(ethoxycarbonylamino)-1-butanol

Ethyl chloroformate (4.7 mL, 49.5 mmol) was added dropwise to a stirred cooled (–40° C.) solution of 3-(4-chlorophenyl)-4-amino-1-butanol (9.0 g, 45 mmol) and triethylamine (7.2 mL, 51.8 mmol) in DCM (125 mL). The solution was stirred at room temperature for 30 min and poured into 1N HCl (60 mL). The organic layer was washed with 1N HCl (70 mL), saturated sodium bicarbonate (70 mL) and saturated sodium chloride; dried (MgSO$_4$), filtered and the solvent removed to provide the title compound (11.4 g, 93%) as a yellow oil. 1H-NMR (CDCl$_3$): δ 1.18–1.23 (t, 3H CH) 1.75–1.84 (m, 1H, CH) 1.90–1.99 (m, 1H, CH) 2.94–2.99 (m, 1H, CH) 3.21–3.30 (m, 1H, CH) 3.47–3.65 (m, 3H, CH) 4.04–4.11 (q, 2H, CH) 4.58 (s, 1H, OH or NH) 7.12–7.15 (d, 2R, ArH) 7.26–7.37 (m, 2H, ArH); MS m/z 272 (M+H).

(e) 3-(4-Chlorophenyl)-4-N-methylamino-1-butanol

This material has been reported (H. Kubota, A. Kafefuda, H. Nagaoka, O. Yamamoto, K. Ikeda, M. Takeuchi, T. Shibanuma, Y. Isomura, Chem. Pharm. Bull., 46(2), 242–254 (1998)); however, the preparation was not exemplified and is therefore presented here. To a stirred cooled (0° C.) mixture of lithium aluminum hydride (3.36 g, 93 mmol) and THF (55 mL) was added dropwise a solution 3-(4-chlorophenyl)-4-(ethoxycarbonylamino)-1-butanol (11.4 g, 42 mmol) in THF (110 mL). The mixture was heated under reflux for 1 h, cooled (ice bath) and saturated sodium sulfate (14 mL) was added. The mixture was stirred at room temperature for 30 min and sodium sulfate (14 g) was added. The mixture was stirred at room temperature for 30 min, filtered through diatomaceous earth, washed with THF, and the filtrate concentrated in vacuo. Chromatography (1–10% methanol in DCM) provided the title compound (5.85 g, 65%) as a yellow oil. $^1$H-NMR (CDCl$_3$) δ 1.86–1.94 (m, 2H, CH) 2.44 (s, 3H, CH) 2.69–2.86 (m, 5H, CH, OH and NH) 3.51–3.58 (m, 1H, CH) 3.66–3.77 (m, 1H, CH) 7.09–7.12 (d, 2H, CH) 7.25–7.29 (d, 2H, CH). MS m/z 214 (M+H).

(f) N-[2-(4-Chlorophenyl)-4-hydroxybutyl]-N-methyl-5,6,7,8-tetrahydro-1-naphthamide To a stirred cooled (0° C.) mixture of 3-(4-chloropenyl)-N-methyl-4-amino-1-butanol (0.706 g, 3.30 mmol) in DCM (25 mL) and 1N NaOH (4.13 mL) was added dropwise a solution of 5,6,7,8-tetrahydro-1-naphthalenecarbonyl chloride (0.643 g, 3.30 mmol) in DCM (10 mL). The mixture was stirred at 0° C. for 2.5 h, H$_2$O and DCM were added and the mixture was extracted with DCM (2×20 mL). The combined organic layers were dried (MgSO$_4$), filtered, and concentrated in vacuo. Purification by chromatography (0%, 50%, 100% EtOAc in Et$_2$O) provided the title compound (1.11 g, 90%) as a solid. MS m/z 372 (M+H).

(g) N-[2-(4-chlorophenyl)-4-oxobutyl]-N-methyl-5,6,7,8-tetrahydro-1-naphthamide

To a stirred cooled (–78° C.) solution of oxalyl chloride (0.39 mL, 4.47 mmol) in DCM (10 mL) was added DMSO (0.64 mL, 9.00 mmol) in DCM (5 mL) dropwise. The solution was stirred at –78 ° C. for 5 min and a solution of N-[2-(4-chlorophenyl)-4-hydroxybutyl]-N-methyl-5,6,7,8- tetrahydro-1-naphthamide (1.11 g, 2.98 mmol) in DCM (6.0 mL) and DMSO (3.4 mL) was added dropwise. The solution was stirred at −78 ° C. for 15 min and triethylamine (2.50 mL, 17.9 mmol) was added. Stirring was continued at −78 ° C. for 30 min and then at room temperature for 2 h. 1N NCl (75 mL) and DCM (75 mL) were added, the layers separated, and the organic layer was dried (MgSO$_4$), filtered, and concentrated in vacuo. Purification by chromatography (silica gel; 50% Et$_2$O/DCM) provided the title compound (1.10 g, 95%) as a tacky solid. MS rm/z 370 (M+H).

EXAMPLE 16

N-(4-[4-(Tetrahydro-2-oxo-1(2H)-pyrimidinyl)-1-piperidinyl]-2-(4-chlorophenyl)-butyl)-N-methyl-5,6,7,8-tetrahydro-1-naphthamide Using standard reductive amination conditions N-[2-(4-chlorophenyl)-4-oxobutyl]-N-methyl-5,6,7,8-tetrahydro-1-naphthamide was reacted with with 4-(tetrahydro-2-oxo-1(2H)-pyrimidinyl)piperidine and converted to the citrate salt. MS: m/z 537 (M+H). Analysis for C$_3$H$_{41}$ClN$_4$O$_2$·C$_6$H$_8$O$_7$·H$_2$O: calculated: C, 59.36; H, 6.87; N, 7.46; found: C, 59.42; H, 6.71; N, 7.12.

EXAMPLE 17

N-(4-[4-(Tetrahydro-2-oxo-1(2H)-pyrimidinyl)-4-(methylaminocarbonyl)-1-piperidinyl]-2-(4-chlorophenyl)-butyl)-N-methyl-5,6,7,8-tetrahydro-1-naphthamide Using standard reductive amination conditions N-[2-(4-chlorophenyl)-4-oxobutyl]-N-methyl-5,6,7,8-tetrahydro-1-naphthamide was reacted with N-(4-[4-(tetrahydro-2-oxo-1(2H)-pyrimidinyl)-4-(methylaminocarbonyl)1-piperidine (Miller, S C; WO 9512577) and converted to the citrate salt. MS: m/z 594 (M+H). Analysis for C$_{33}$H$_{44}$ClN$_5$O$_3$·C$_6$H$_8$O$_7$·1.1H$_2$O: calculated: C, 58.11; H, 6.78; N, 8.69; found: C, 58.01; H, 6.70; N, 8.44.

EXAMPLE 18

Following conventional procedures well known in the pharmaceutical art the following representative pharmaceutical dosage forms containing a compound of the formula I) can be prepared:

a) Tablet

| (a) Tablet | mg/tablet |
|---|---|
| Compound of Formula I | 50.0 |
| Lactose, USP | 223.75 |
| Croscarmellose sodium | 60.0 |
| Maize starch | 15.0 |
| Hydroxypropylmethylcellulose (HPMC), USP | 2.25 |
| Magnesium stearate | 3.0 |

| (b) Capsule | mg/capsule |
|---|---|
| Compound of Formula I | 10.0 |
| Lactose, USP | 488.5 |
| Croscarmellose sodium | 15.0 |
| Magnesium stearate | 1.5 |

(c) Injection

For intravenous administration, a compound of Formula I is dissolved in an isotonic sterile solution (5 mg/mL).

What is claimed is:

1. A compound of the formula (I):

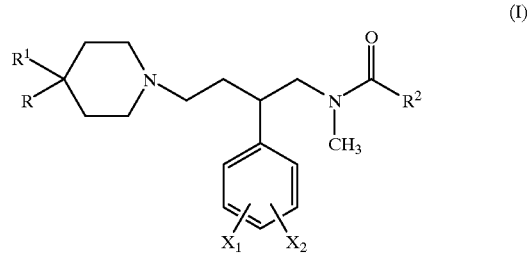

wherein:
R is hydrogen, hydroxy, C$_{1-6}$alkoxy, C$_{1-6}$alkanoyloxy, C$_{1-6}$alkanoyl, C$_{1-6}$alkoxycarbonyl, C$_{1-6}$alkanoylamino, C$_{1-6}$alkyl, carbamoyl, C$_{1-6}$alkylcarbamoyl or di-C$_{1-6}$alkylcarbamoyl;

R$^1$ is a phenyl group having an ortho substituent selected from C$_{1-6}$alkylthio, C$_{1-6}$alkylsulfinyl, C$_{1-6}$alkylsufonyl, trifluoromethylthio, trifluoromethylsulfinyl, C$_{1-6}$alkanesulfonamido, C$_{1-6}$alkanoyl, C$_{1-6}$alkoxycarbonyl, succinamido, carbamoyl, C$_{1-6}$alkyl-carbamoyl, di-C$_{1-6}$alkylcarbamoyl, C$_{1-6}$alkoxy-C$_{1-6}$alkylcarbamoyl, C$_{1-6}$alkanoylamino, ureido, C$_{1-6}$ureido, di-C$_{1-6}$alkylureido, amino, C$_{1-6}$alkylamino or di-C$_{1-6}$alkylamino;

and wherein said ortho-substituted phenyl group bears 0, 1, 2 or 3 additional substituents selected from C$_{1-6}$alkylthio, C$_{1-6}$alkylsulfinyl, C$_{1-6}$alkylsulfonyl, carboxy, C$_{1-6}$alkoxycarbonyl, C$_{1-6}$alkanoyl, nitro, amino, C$_{1-6}$alkylamino, di-C$_{1-6}$alkylamino wherein the alkyl groups may be the same or different, CF$_3$S(O)$_x$ wherein x is 0, 1 or 2, C$_{1-6}$alkanoylamino, C$_{1-6}$alkylsulphonamido, ureido, C$_{1-6}$alkylureido, di-C$_{1-6}$alkylureido, carbamoyl, C$_{1-6}$alkylcarbamoyl, di-C$_{1-6}$alkylcarbamoyl wherein the alkyl groups may be the same or different and C$_{1-6}$alkyl; or R$^1$ is a group of the formula (Ia):

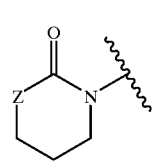

wherein Z is NH or CH$_2$;

R$^2$ is 5,6,7,8-tetrahydronaphth-1-yl, which is unsubstituted or substituted with substituents selected from hydroxy, cyano, nitro, trifluoromethoxy, trifluoromethyl, C$_{1-6}$alkysulfonyl, halo, C$_{1-6}$alkoxy, methylenedioxy, C$_{1-6}$alkyl, C$_{2-6}$alkenyl, C$_{2-6}$alkynyl, carboxy, C$_{1-6}$alkoxy-carbonyl, C$_{1-6}$alkylcarbamoyl, di-C$_{1-6}$alkylcarbamoyl, C$_{1-6}$alkanoyl, C$_{1-6}$alkanoylamino, aminosulfonyl and C$_{1-6}$alkyl; and X$_1$ and X$_2$ are independently hydrogen or halo, provided that at least one of X$_1$ or X$_2$ is halo; or pharmaceutically acceptable salts thereof.

2. A compound according to claim 1, wherein:
R is hydrogen, hydroxy, methoxycarbonyl, methylcarbonyl or dimethylcarbamoyl; and
R$^1$ is a phenyl having an ortho substituent selected from methylsulfinyl, ethylsulfinyl), propylsulfinyl, methylsulfonyl, trifluoromethylthio, trifluormethylsulfinyl, methanesulfonamido, acetyl, methoxycarbonyl, succiniamido, carbamoyl, methylcarbamoyl, dimethylcarbamoyl, N-methylcarbamoyl, acetylamino, ureido, methylureido, dimethylureido, amino, methylamino and dimethylamino.

3. A compound according to claim 1, wherein:

R is hydrogen or hydroxy; and $R^1$ is a phenyl having an ortho substituent selected from methylsulfinyl, methylsulfonyl, methylureido, dimethylureido, amino, methylamnino and dimethylamino.

4. A compound according claim 1, wherein:

the ortho-substituted phenyl group is unsubstituted, or is substituted by a para substituent selected from methyl, acetyl, acetylamino, methoxycarbonyl, methanesulfonylamino, methyl-sulfinyl, methylsulfonyl, trifluoromethylthio, triflouromethylsulfinyl, carbamoyl, methylcarbamoyl, dimethlylcarbarmoylmethylureido and dimethylureido.

5. A compound according to claim 1 wherein:

$R^2$ is unsubstituted or substituted by 1 or 2 substituents selected from cyano, methoxy, ethoxy, isopropoxy, fluoro, bromo, chloro, iodo, nitro, cyanomethyl, carboxy, carbamoyl, ethynyl, methyl, dimethylcarbamoyl, methylsulfonyl, aminosulfonyl, prop-2-enyl, acetyl and acctylamino.

6. A compound according to claim 5, wherein:

$R^2$ is unsubstituted or substituted by 1 or 2 substituents selected from cyano, methoxy, flouro and nitro.

7. A compound according to claim 1, wherein the compound is selected from:

N-[2-(S)-(3,4-dichlorophenyl)4-[4-[(S)-2-(methylsulfinyl)phenyl]-1-piperidinyl]butyl]-N-methyl-3-cyano-2-methyl-5,6,7,8-tetrahydro-1-naphthamide;

N-[2-(S)-(3,4-dichlorophenyl)-4-[4-[(S)-2-(methylsulfinyl)phenyl]-1-piperidinyl]butyl]-N-methyl-3-cyano-2-ethyl-5,6,7,8-tetrahydro-1-naphthamide;

N-[2-(S)-(3,4-dichlorophenyl)-4-[4-[(S)-2-(methylsulfinyl)phenyl]-1-piperidinyl]butyl]-N-methyl-3-methoxy-2-methyl-5,6,7,8-tetrahydro-1-naphthamide;

N-[2-(S)-(3,4-dichlorophenyl)-4-[4-[(S)-2-(methylsulfinyl)phenyl]-1-piperidinyl]butyl]-N-methyl-2-methoxy-3-methyl-5,6,7,8-tetrahydro-1-naphthamide;

N-[2-(S)-(3,4-dichlorophenyl)-4-[4-[(S)-2-(methylsulfinyl)phenyl]-1-piperidinyl]butyl]-N-methylsulfonyl-3-cyano-2-methoxy-5,6,7,8-tetrahydro-1-naphthamide; and N-(4-[4-(tetrahydro-2-oxo-1(2H)-pyrimidinyl)-4-methylaminocarbonyl)-1-piperidinyl]-2-(3,4-dichlorophenyl)butyl)-N-methyl-3-cyano-2-methoxy-5,6,7,8-tetrahydro-1-naphthamide.

8. A pharmaceutical composition comprising:

a therapeutically-effective amount of a compound according to claim 1; and a pharmaceutically-acceptable diluent or carrier.

9. A method of treating a disease selected from asthma, anxiety, depression, emesis and urinary incontinence comprising the step of administering a therapeutically-effective amount of a compound according to claim 1.

* * * * *